US010561722B2

(12) United States Patent
Volkmann et al.

(10) Patent No.: US 10,561,722 B2
(45) Date of Patent: *Feb. 18, 2020

(54) METHODS AND COMPOSITIONS FOR ENHANCING IMMUNE RESPONSES

(71) Applicants: Bavarian Nordic A/S, Kvistgaard (DK); Janssen Vaccines & Prevention B.V., Leiden (NL); The United States of America, as represented by The Secretary, Department of Health and Human Services, Bethesda, MD (US)

(72) Inventors: Ariane Volkmann, Andechs (DE); Robin Steigerwald, Munich (DE); Ulrike Dirmeier, Starnberg (DE); Benoit Christophe Stephan Callendret, Leiden (NL); Macaya Julie Douoguih, Leiden (NL); Lucy A. Ward, Silver Spring, MD (US)

(73) Assignees: Bavarian Nordic A/S, Kvistgaard (DK); Janssen Vaccines & Prevention B.V., Leiden (NL); The United States of America, as represented by The Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/508,288

(22) PCT Filed: Sep. 3, 2015

(86) PCT No.: PCT/US2015/048388
§ 371 (c)(1),
(2) Date: Mar. 2, 2017

(87) PCT Pub. No.: WO2016/036971
PCT Pub. Date: Mar. 10, 2016

(65) Prior Publication Data
US 2017/0340721 A1    Nov. 30, 2017

Related U.S. Application Data

(60) Provisional application No. 62/189,109, filed on Jul. 6, 2015, provisional application No. 62/159,823, filed on May 11, 2015, provisional application No. 62/116,021, filed on Feb. 13, 2015, provisional application No. 62/045,522, filed on Sep. 3, 2014.

(51) Int. Cl.
*A61K 39/12* (2006.01)
*C12N 15/861* (2006.01)
*C12N 15/863* (2006.01)
*A61K 39/00* (2006.01)

(52) U.S. Cl.
CPC ...... *A61K 39/12* (2013.01); *A61K 2039/5256* (2013.01); *A61K 2039/545* (2013.01); *C12N 15/861* (2013.01); *C12N 15/863* (2013.01); *C12N 2710/24043* (2013.01); *C12N 2760/14234* (2013.01)

(58) Field of Classification Search
None
See application file for complete search history.

(56) References Cited

U.S. PATENT DOCUMENTS

| 5,185,146 A | 2/1993 | Altenburger |
| 6,083,716 A | 7/2000 | Wilson et al. |
| 6,761,893 B2 | 7/2004 | Chaplin et al. |
| 7,270,811 B2 | 9/2007 | Bout et al. |
| 9,526,777 B2 * | 12/2016 | Sullivan ............... A61K 39/12 |
| 2003/0206926 A1 | 11/2003 | Chaplin et al. |
| 2006/0159699 A1 | 7/2006 | Howley et al. |
| 2010/0247522 A1 * | 9/2010 | Zhang ................ A61K 39/29 424/131.1 |
| 2013/0101618 A1 | 4/2013 | Sullivan et al. |
| 2014/0017278 A1 | 1/2014 | Sullivan et al. |
| 2015/0361141 A1 * | 12/2015 | Buttigieg ............. A61K 39/12 424/186.1 |

FOREIGN PATENT DOCUMENTS

| JP | 2005517639 A | | 6/2005 |
| JP | 2014503206 A | | 2/2014 |
| WO | WO 2000/00616 | * | 1/2000 |
| WO | WO 2000/08131 | * | 2/2000 |

(Continued)

OTHER PUBLICATIONS

Barouch et al, "Vaccine Protection Against Acquisition of Neutralization-Resistant SIV Challenges in Rhesus Monkeys," Nature, vol. 482, No. 7383, pp. 89-93 (Feb. 2012).
Gilbert et al, "Enhanced CD8 T Cell Imunnogenicity and Protective Efficacy in a Mouse Malaria Model Using a Recombinant Adenoviral Vaccine in Heterologous Prime-Boost Immunisation Regimes," Vaccine, vol. 20, No. 7-8, pp. 1039-1045 (2002).
Roshorm et al, "T Cells Induced by Recombinant Chimpanzee Adenovirus Alone and in Prime-Boost Regimens Decrease Chimeric EcoHIV/NDK Challenge Virus Load," European Jounral of Immunology, vol. 42, No. 12, pp. 3243-3255 (2012).

(Continued)

*Primary Examiner* — Nicole Kinsey White
(74) *Attorney, Agent, or Firm* — Panitch Schwarze Belisario & Nadel LLP

(57) ABSTRACT

Compositions and methods are described for generating an improved effective immune response against an immunogen in humans. The enhanced immune response, is obtained by using an MVA vector as a prime and an adenovirus vector as a boost and is characterized by a high level of antibody response specific to the immunogen, and an enhanced cellular immune response. The compositions and methods can be used to provide a protective immunity against a disease, such as an infection of one or more subtypes of Ebola and Marburg filoviruses, in humans.

20 Claims, 20 Drawing Sheets
(16 of 20 Drawing Sheet(s) Filed in Color)
Specification includes a Sequence Listing.

(56) References Cited

FOREIGN PATENT DOCUMENTS

| WO | 2000/070071 A1 | | 11/2000 |
|---|---|---|---|
| WO | 2002/024224 A2 | | 3/2002 |
| WO | 2002/042480 A2 | | 5/2002 |
| WO | 2003/048184 A2 | | 6/2003 |
| WO | 2003047617 A2 | | 6/2003 |
| WO | 2003/104467 A1 | | 12/2003 |
| WO | 2004/001032 A2 | | 12/2003 |
| WO | 2005/071093 A2 | | 8/2005 |
| WO | 2006/037038 A1 | | 4/2006 |
| WO | 2007/104792 A2 | | 9/2007 |
| WO | WO 2010/057650 | * | 5/2010 |
| WO | 2010/085984 A1 | | 8/2010 |
| WO | 2010/086189 A2 | | 8/2010 |
| WO | 2011/092029 A1 | | 8/2011 |
| WO | 2012/082918 A1 | | 6/2012 |
| WO | WO 2012/106490 | * | 8/2012 |
| WO | WO 2013/155441 | * | 10/2013 |
| WO | 2014006191 A1 | | 1/2014 |
| WO | 2014/037124 A1 | | 3/2014 |

OTHER PUBLICATIONS

Subbotina et al, "Genetic Factors of Ebola Virus Virulence in Guinea Pigs," Virus Research, vol. 153, No. 1, pp. 121-133 (2010).

Sanchez et al, "Analysis of Human Peripheral Blood Samples from Fatal and Nonfatal Cases of Ebola (Sudan) Hemorrhagic Fever: Cellular Responses, Virus Load and Nitric Oxide Levels," Jounral of Virology, vol. 78, No. 19, pp. 10370-10377 (2004).

Towner et al, "Marburgvirus Genomics and Association with a Large Hemorrhagic Fever Outbreak in Angola," Jounral of Virology, vol. 80, No. 13, pp. 6497-6516 (2006).

Enterlein et al, "Rescue of Recombinant Marburg Virus from cDNA is Dependent on Nucleocapsid Protein VP30," Jounral of Virology, vol. 80, No. 2, pp. 1038-1043 (2006).

Towner et al, "Newly Discovered Ebola Virus Associated With Hemorrhagic Fever Outbreak in Uganda," PLOS Pathogens Public Library of Science, US, vol. 4, No. 11, pp. 1-6 (2008).

Geisbert et al, "Recombinant Adenovirus Serotype 26 (Ad26) and Ad35 Vaccine Vectors Bypass Immunity to Ad5 and Protect Nonhuman Primates Against Ebolavirus Challenge," Jounral of Virology, vol. 85, No. 9, pp. 4222-4233 (2011).

Wang et al, "De Novo Syntheses of Marburg Virus Antigens From Adenovirus Vectors Induce Potent Humoral and Cellular Immune Response," Vaccine, vol. 24, No. 15, pp. 2975-2986 (2006).

Int'l Preliminary Report on Patentability dated Mar. 7, 2017 in Int'l Application No. PCT/US2015/048357.

Int'l Search Report dated Nov. 1, 2016 in Int'l Application No. PCT/US2015/048357.

Sanchez et al., "The virion glycoproteins of Ebola viruses are encoded in two reading frames and expressed through transcriptional editing," PNAS USA, vol. 93, No. 8, pp. 3602-3607 (1996).

Friedrich et al., "Potential vaccines and post-exposure treatments for filovirus infections," Viruses, vol. 4, No. 9, pp. 1619-1650 (2012).

Hill et al., "Prime-boost vectored malaria vaccines: progress and prospects," Human Vaccines, vol. 6, No. 1, pp. 78-83 (2010).

Sullivan et al., "Immune protection of nonhuman primates against Ebola Virus with single low-dose adenovirus vectors encoding modified GPs," PLoS Medicine, vol. 3, No. 6, pp. 177 (2006).

Radosevic et al., "Protective immune responses to a recombinant adenovirus type 35 tuberculosis vaccine in two mouse strains: CD4 and CD8 T-cell epitope mapping and role of gamma interferon," Inf. Immun., vol. 75, No. 8, pp. 4105-4115 (2007).

Santra et al., "Heterologous prime/boost immunizations of rhesus monkeys using chimpanzee adenovirus vectors," Vaccine, vol. 27, No. 42, pp. 5837-5845 (2009).

Asmuth et al., "Comparative cell-mediated immunogenicity of DNA/DNA, DNA/Adenovirus Type 5 (Ad5), or Ad5/Ad5 HIV-1 Clade B gag Vaccine Prime-Boost regimens," J. Infect. Dis., vol. 201, pp. 132-141 (2010).

Kibuuka et al., "A phase 1/2 study of a multiclade HIV-1 DNA plasmid prime and recombinant adenovirus 5 boost vaccine in HIV-uninfected east Africans (RV 172)," J. Infect. Dis., vol. 201, pp. 600-607 (2010).

Koup et al., "Priming immunization with DNA augments immunogenicity of recombinant adenoviral vectors for both HIV-1 specific antibody and T-cell responses," PLoS One, vol. 5, No. 2, pp. 9015 (2010).

Catanzaro et al., "Phase 1 safety and immunogenicity evaluation of a multiclade HIV-1 candidate vaccine delivered by a replication-defective recombinant adenovirus vector," J. Infect. Dis., vol. 194, No. 12, pp. 1638-1649 (2006).

Harro et al., "Safety and immunogenicity of the Merck Adenovirus serotype 5 (MRKAd5) and MRKAd6 Human Immunodeficiency Virus Type 1 trigene vaccines alone and in combination in healthy adults," Clin. Vaccine Immunol., vol. 16, No. 9, pp. 1285-1292 (2009).

Cheng et al., "Mechanism of Ad5 vaccine immunity and toxicity: fiber shaft targeting of dendritic cells," PLoS Pathogens, vol. 3, No. 2, pp. 25 (2007).

McCoy et al., "Effect of preexisting immunity to adenovirus human serotype 5 antigens on the immune responses of nonhuman primates to vaccine regimens based on human-or chimpanzee-derived adenovirus vectors," J. Virol., vol. 81, No. 12, pp. 6594-6604 (2007).

Abbink et al., "Comparative seroprevalence and immunogenicity of six rare serotype recombinant adenovirus vaccine vectors from subgroups B and D," J. Virol., vol. 81, No. 9, pp. 4654-4663 (2007).

Havenga et al., "Novel replication-incompetent adenoviral B-group vectors: high vector stability and yield in PER.C6 cells," J. Gen. Virol., vol. 87, pp. 2135-2143 (2006).

De Gruijl et al., "Intradermal delivery of adenoviral type-35 vectors leads to high efficiency transduction of mature, CD8+ T cell-stimulating skin-emigrated dendritic cells," J. Immunol., vol. 177, pp. 2208-2215 (2006).

Lore et al., "Myeloid and plasmacytoid dendritic cells are susceptible to recombinant adenovirus vectors and stimulate polyfunctional memorty T cell responses," J. Immunol., vol. 179, pp. 1721-1729 (2007).

Haslett et al., "Strong human immunodeficiency virus (HIV)-specific CD4+ T cell responses in a cohort of chronically infected patients are associated with interruptions in anti-HIV chemotherapy," J. Infect. Dis., vol. 181, pp. 1264-1272 (2000).

Harrer et al., "Therapeutic vaccination of HIV-1-infected patients on HAART with a recombinant HIV-1 nef-expressing MVA: safety, immunogenicity and influence on viral load during treatment interruption," Antivir. Ther., vol. 10, No. 2, pp. 285-300 (2005).

Di Nicola et al., "Boosting T cell-mediated immunity to tyrosinase by vaccinia virus-transduced, CD34+-derived dendritic cell vaccination: a phase I trial in metastatic melanoma," Clin. Cancer Res., vol. 10, No. 16, pp. 5381-5390 (2004).

Peters et al., "Filoviruses as emerging pathogens," Seminars in Virology, vol. 5, pp. 147-154 (1994).

Vogels et al., "Replication-deficient human adenovirus type 35 vectors for gene transfer and vaccination: efficient human cell infection and bypass of preexisting adenovirus immunity," J. Virol., vol. 77, No. 15, pp. 8263-8271 (2003).

Farina et al., "Replication-defective vector based on a Chimpanzee adenovirus," J. Virol., vol. 75, pp. 11603-11613 (2001).

Cohen et al., "Chimpanzee adenovirus CV-68 adapted as a gene delivery vector interacts with the coxsackievirus and adenovirus receptor," J. Gen. Virol., vol. 83, pp. 151-155 (2002).

Kobinger et al., "Chimpanzee adenovirus vaccine protects against Zaire Ebola virus," Virology, vol. 346, pp. 394-401 (2006).

Tatsis et al., "A CD46-binding Chimpanzee Adenovirus Vector as a Vaccine Carrier," Mol. Ther., vol. 15, pp. 608-617 (2007).

Lasaro et al, "New Insights on Adenovirus as Vaccine Vectors," Mol. Ther. vol. 17, pp. 1333-1339 (2009).

Blanchard et al., "Modified vaccinia virus ankara undergoes limited replication in human cells and lacks several immunomodulatory proteins: implications for use as a human vaccine," J. Gen. Virol., vol. 79, pp. 1159-1167 (1998).

Carroll et al, "Host range and cytopathicity of the highly attenuated MVA strain of vaccinia virus: propagation and generation

(56) References Cited

OTHER PUBLICATIONS of recombinant viruses in a nonhuman mammalian cell line," Virology, vol. 238, pp. 198-211 (1997).
Ambrosini et al., "Gene transfer in astrocytes: comparison between different delivering methods and expression of the HIV-1 protein Nef," J. Neurosci. Res., vol. 55, pp. 569-577 (1999).
Boukamp et al., "Normal keratinization in a spontaneously immortalized aneuploidy human keratinocyte cell line," J. Cell Biol., vol. 106, pp. 761-771 (1988).
Shiver et al., "Replication-incompetent adenoviral vaccine vector elicits effective anti-immunodeficiency-virus immunity," Nature, vol. 415, pp. 331-335 (2002).
Sullivan et al., "Development of a preventive vaccine for Ebola virus infection in primates," Nature, vol. 408, pp. 605-609 (2000).
Sullivan et al., "Accelerated vaccination for Ebola virus haemorrhagic fever in non-human primates," Nature, vol. 424, pp. 681-684 (2003).
Buchbinder et al., "Efficacy assessment of a cell-mediated immunity HIV-1 vaccine (the Step Study): a double-blind, randomized, placebo-controlled, test-of-concept trial," Lancet, vol. 372, pp. 1881-1893 (2008).
Liu et al., "Immune control of an SIV challenge by a T-cell-based vaccine in rhesus monkeys," Nature, vol. 457, pp. 87-91 (2009).
Jin et al., "Stabilizing formulations for inhalable powders of an adenovirus 35-vectored tuberculosis (TB) vaccine (AERAS-402)," Vaccine, vol. 28, No. 27, pp. 4369-4375 (2010).
Cosma et al., "Therapeutic vaccination with MVA-HIV-1 nef elicits Nef-specific T-helper cell responses in chronically HIV-1 infected individuals," Vaccine, vol. 22, No. 1, pp. 21-29 (2005).
Di Nicola et al., "Immunization of patients with malignant melanoma with autologous CD34+ cell-derived dendritic cells transduced ex vivo with a recombinant replication-deficient vaccinia vector encoding the human tyrosinase gene: a phase I trial," Hum. Gene Ther., vol. 14, No. 14, pp. 1347-1360 (2004).
Bangari et al., "Development of nonhuman adenoviruses as vaccine vectors," Vaccine, vol. 24, pp. 849-862 (2006).
Mayr et al., "Passage history, properties and applicability of the attenuated vaccinia virus strain MVA," Infection, vol. 3, pp. 6-14 (1975).
Mayr et al., "Vaccination against pox diseases under immunosuppressive conditions," Dev. Biol. Stand., vol. 41, pp. 225-234 (1978).
Stickl, "Smallpox vaccination and its consequences: first experiences with the highly attenuated smallpox vaccine MVA," Prev. Med., vol. 3, pp. 97-101 (1974).
Stickl et al., "Intracutaneous smallpox vaccination with a weak pathogenic vaccinia virus ('MVA virus')," Munch. Med. Wochenschr., vol. 113, pp. 1149-1153 (1971).
Mayr et al., "The Smallpox Vaccination Strain MVA : Marker, Genetic Structure, Experience Gained with the Parenteral Vaccination and Behavior in Organisms with a Debilitated Defence Mechanism," Zentralbl. Bacteriology, vol. 167, pp. 375-390 (1978).
Peters et al., "Filoviridae: Marburg and Ebola Viruses", Eds., Fields Virology, 3rd Edition, pp. 1161-1176 (1996).
Ophorst et al., "Increased Immunogenicity of Recombinant Ad35-based Malaria Vaccine Through Formulation with Aluminum Phosphate Adjuvant," Vaccine, vol. 25, pp. 6501-6510 (2007).
Lee et al, "Recent Advances of Vaccine Adjuvants for Infectious Diseases," Immune Network, vol. 15, No. 2, pp. 51-57 (2015).
Butterfield et al., "Cancer vaccines," BMJ, vol. 350, pp. h988 (2015).
Fenoglio et al, "Generation of more effective cancer vaccines," Hum. Vaccine Immunother., vol. 9, No. 12, pp. 2543-2547 (2013).
Swain et al., "Expanding roles for CD4+ T cells in immunity to viruses," Nat. Rev. Immunol., vol. 12, No. 2, pp. 136-148 (2012).
Sant et al, "Revealing the role of CD4+ T cells in viral immunity," J. Exp. Med., vol. 209, No. 8, pp. 1391-1395 (2012).
Wilkinson et al., "Preexisting influenza-specific CD4+ T cells correlate with disease protection against influenza challenge in humans," Nat. Med., vol. 18, No. 2, pp. 274-280 (2012).
Int'l Preliminary Report on Patentability dated Mar. 7, 2017 in Int'l Application No. PCT/US2015/048388.
Int'l Search Report dated Nov. 1, 2016 in Int'l Application No. PCT/US2015/048388.
Altenburg et al., "Modified Vaccinia Virus Ankara (MVA) as Production Platform for Vaccines against Influenza and other Viral Respiratory Diseases" Viruses, vol. 6, pp. 2735-2761, 2014.
Lu, "Heterologous Prime-Boost Vaccination", Curr Opin Immunol, 21(3), pp. 346-351, Jun. 2009.
NCBI Genbank Accession No. NP_066246.1 (Feb. 10, 1999).
NCBI Genbank Accession No. Q1PD50 (Oct. 31, 2006).
NCBI Genbank Accession No. YP_001531156.1 (Oct. 23, 2007).
NCBI Genbank Accession No. YP_003815423.1 (Aug. 5, 2010).
NCBI Genbank Accession No. YP_138523.1 (Nov. 15, 2004).

* cited by examiner

| Group | N | Administration of test or control article | | | | EBOLA Challenge (Day) |
|---|---|---|---|---|---|---|
| | | Prime | Boost(s) | Dose | Schedule (Day) | |
| A | 2 | Neg Control (Ad26.empty) | Neg Control (MVA.empty) | $1.2 \times 10^{11}$ vp/ $5 \times 10^8$ TCID50 | 0, 56 | Day 84 Ebola Kikwit i.m. 100 pfu (approx 4 weeks after last immunization) |
| B | 2 | Ad26.ZEBOV | Ad35.ZEBOV | $1.2 \times 10^{11}$ vp | 28, 56 | |
| C | 2 | Ad26.MARVA Ad26.SEBOV Ad26.ZEBOV | MVA-Multi | $4 \times 10^{10}$ vp (each)/ $5 \times 10^8$ TCID50 | 0, 56 | |
| D | 2 | MVA-Multi | Ad26.MARVA Ad26.SEBOV Ad26.ZEBOV | $5 \times 10^8$ TCID50/ $4 \times 10^{10}$ vp (each) | 0, 56 | |
| E | 2 | Ad26.MARVA Ad26.SEBOV Ad26.ZEBOV | Ad26.MARVA Ad26.SEBOV Ad26.ZEBOV MVA-Multi | $4 \times 10^{10}$ vp (each)/ $5 \times 10^8$ TCID50 | 0, 28, 56 | |

Cellular Response (ICS): Functionality of CD8 responses
Ad26.ZEBOV/MVA-BN-Filo 0, 56 day schedule
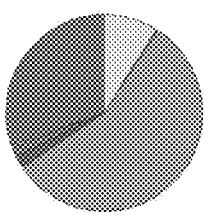 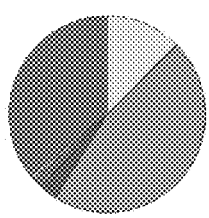 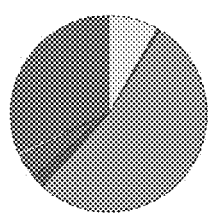
d57　　　　　　　　d64　　　　　　　　d78
MVA-BN-Filo/Ad26.ZEBOV 0, 56 day schedule
NA 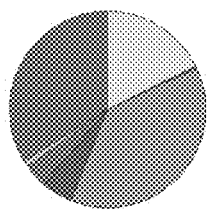 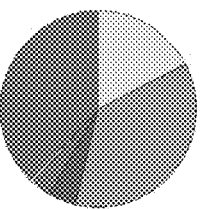
d57　　　　　　　　d64　　　　　　　　d78
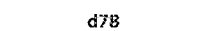
Figure 12

Cellular Response (ICS): Functionality of CD4 responses
Ad26.ZEBOV/MVA-BN-Filo 0, 28 day schedule
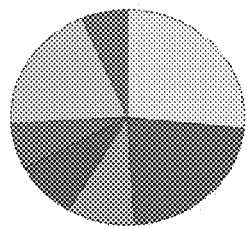
d29
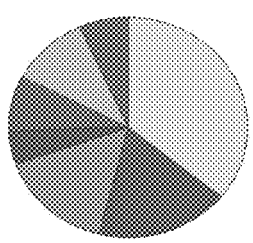
d36
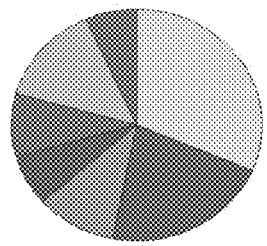
d50
MVA-BN-Filo/Ad26.ZEBOV 0, 28 day schedule
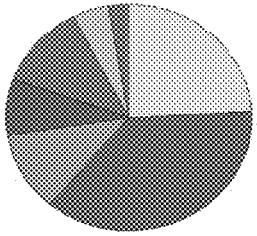
d29
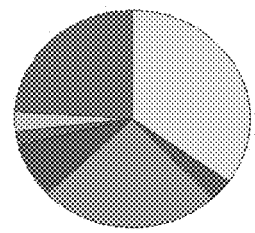
d36
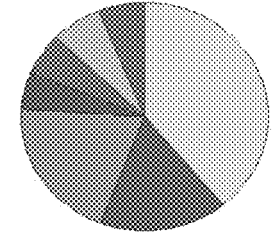
d50
Figure 14

Cellular Response (ICS): Functionality of CD4 responses
Ad26.ZEBOV/MVA-BN-Filo 0, 56 day schedule
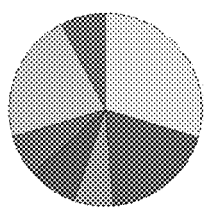 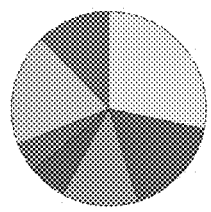 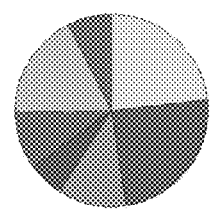
d57         d64         d78
MVA-BN-Filo/Ad26.ZEBOV 0, 56 day schedule
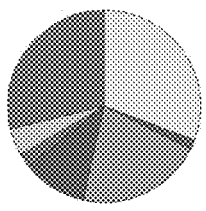 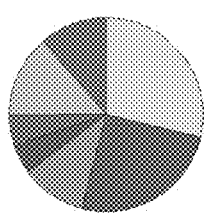
d57         d64         d78
Figure 15

METHODS AND COMPOSITIONS FOR ENHANCING IMMUNE RESPONSES

CROSS REFERENCE TO RELATED APPLICATIONS

This application is a Section 371 of International Application No. PCT/US15/48388, which was published in the English Language on Mar. 10, 2016, under International Publication No. WO/2016/036971, which claims priority to U.S. Provisional Application No. 62/189,109, filed on Jul. 6, 2015; U.S. Provisional Application No. 62/159,823, filed on May 11, 2015; U.S. Provisional Application No. 62/116,021, filed on Feb. 13, 2015; and U.S. Provisional Application No. 62/045,522, filed on Sep. 3, 2014. Each disclosure is incorporated herein by reference in its entirety.

STATEMENT REGARDING FEDERALLY SPONSORED RESEARCH OR DEVELOPMENT

This invention was made with government support under Contract Nos. HESN272201200018C and HESN272200800056C awarded by the National Institute of Allergy and Infectious Disease, a component of the National Institutes of Health, an agency of the Department of Health and Human Services. The government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "689206-2US Sequence Listing" and a creation date of Feb. 27, 2017, and having a size of 30 kB. The sequence listing submitted via EFS-Web is part of the specification and is herein incorporated by reference in its entirety.

FIELD OF THE INVENTION

This invention relates to methods and compositions for enhancing an immune response in a human subject. In particular, the methods and compositions provide a strong induction of B cell and T cell activity against an immunogen in a human subject, which can be used to provide an effective treatment and/or protection against a disease, such as a tumor or an infectious disease, more particularly an infection by a filovirus, in the human subject.

BACKGROUND OF THE INVENTION

Vaccines can be used to provide immune protection against pathogens, such as viruses, bacteria, fungi, or protozoans, as well as cancers.

Infectious diseases are the second leading cause of death worldwide after cardiovascular disease but are the leading cause of death in infants and children (Lee and Nguyen, 2015, Immune Network, 15(2):51-7). Vaccination is the most efficient tool for preventing a variety of infectious diseases. The goal of vaccination is to generate a pathogen-specific immune response providing long-lasting protection against infection. Despite the significant success of vaccines, development of safe and strong vaccines is still required due to the emergence of new pathogens, re-emergence of old pathogens and suboptimal protection conferred by existing vaccines. Recent important emerging or re-emerging diseases include: severe acute respiratory syndrome (SARS) in 2003, the H1N1 influenza pandemic in 2009, and Ebola virus in 2014. As a result, there is a need for the development of new and effective vaccines against emerging diseases.

Cancer is one of the major killers in the Western world, with lung, breast, prostate, and colorectal cancers being the most common (Butterfield, 2015, BMJ, 350:h988). Several clinical approaches to cancer treatment are available, including surgery, chemotherapy, radiotherapy, and treatment with small molecule signaling pathway inhibitors. Each of these standard approaches has been shown to modulate antitumor immunity by increasing the expression of tumor antigens within the tumor or causing the release of antigens from dying tumor cells and by promoting anti-tumor immunity for therapeutic benefit. Immunotherapy is a promising field that offers alternative methods for treatment of cancer. Cancer vaccines are designed to promote tumor-specific immune responses, particularly cytotoxic CD8+ T cells that are specific to tumor antigens. Clinical efficacy must be improved in order for cancer vaccines to become a valid alternative or complement to traditional cancer treatments. Considerable efforts have been undertaken so far to better understand the fundamental requirements for clinically-effective cancer vaccines. Recent data emphasize that important requirements, among others, are (1) the use of multi-epitope immunogens, possibly deriving from different tumor antigens; (2) the selection of effective adjuvants; (3) the association of cancer vaccines with agents able to counteract the regulatory milieu present in the tumor microenvironment; and (4) the need to choose the definitive formulation and regimen of a vaccine after accurate preliminary tests comparing different antigen formulations (Fenoglio et al., 2013, Hum Vaccin Immunother, (12):2543-7). A new generation of cancer vaccines, provided with both immunological and clinical efficacy, is needed to address these requirements.

Ebolaviruses, such as Zaire ebolavirus (EBOV) and Sudan ebolavirus (SUDV), and the closely related Marburg virus (MARV), are associated with outbreaks of highly lethal Ebola Hemorrhagic Fever (EHF) in humans and primates in North America, Europe, and Africa. These viruses are filoviruses that are known to infect humans and non-human primates with severe health consequences, including death. Filovirus infections have resulted in case fatality rates of up to 90% in humans. EBOV, SUDV, and MARV infections cause EHF with death often occurring within 7 to 10 days post-infection. EHF presents as an acute febrile syndrome manifested by an abrupt fever, nausea, vomiting, diarrhea, maculopapular rash, malaise, prostration, generalized signs of increased vascular permeability, coagulation abnormalities, and dysregulation of the innate immune response. Much of the disease appears to be caused by dysregulation of innate immune responses to the infection and by replication of virus in vascular endothelial cells, which induces death of host cells and destruction of the endothelial barrier. Filoviruses can be spread by small particle aerosol or by direct contact with infected blood, organs, and body fluids of human or NHP origin. Infection with a single virion is reported to be sufficient to cause Ebola hemorrhagic fever (EHF) in humans. Presently, there is no therapeutic or vaccine approved for treatment or prevention of EHF. Supportive care remains the only approved medical intervention for individuals who become infected with filoviruses.

As the cause of severe human disease, filoviruses continue to be of concern as both a source of natural infections, and also as possible agents of bioterrorism. The reservoir for filoviruses in the wild has not yet been definitively identified. Four subtypes of Ebolaviruses have been described to cause EHF, i.e., those in the Zaire, Sudan, Bundibugyo and Ivory Coast episodes (Sanchez A. et al., 1996, PNAS USA, 93:3602-3607). These subtypes of Ebolaviruses have similar genetic organizations, e.g., negative-stranded RNA viruses containing seven linearly arrayed genes. The structural gene products include, for example, the envelope glycoprotein that exists in two alternative forms, a secreted soluble glycoprotein (ssGP) and a transmembrane glycoprotein (GP) generated by RNA editing that mediates viral entry (Sanchez A. et al., 1996, PNAS USA, 93:3602-3607).

It has been suggested that immunization can be useful in protecting against Ebola infection because there appears to be less nucleotide polymorphism within Ebola subtypes than among other RNA viruses (Sanchez A. et al., 1996, PNAS USA, 93:3602-3607). Until recently, developments of preventive vaccines against filoviruses have had variable results, partly because the requirements for protective immune responses against filovirus infections are poorly understood. Additionally, the large number of filoviruses circulating within natural reservoirs complicates efforts to design a vaccine that protects against all species of filoviruses.

Currently, there are several vaccine antigen delivery platforms that demonstrated various levels of protection in non-human primates (NHPs) exposed with high infectious doses of filoviruses. Vaccine candidates are in development based on a variety of platform technologies including replication competent vectors (e.g. Vesicular Stomatitis Virus; Rabies virus; Parainfluenza Virus); replication incompetent vectors (Adenovirus, Modified Vaccinia Ankara Virus); protein subunits inclusive of Virus Like Particles expressed in bacterial cells, insect cells, mammalian cells, plant cells; DNA vaccines; and/or live and killed attenuated filovirus (Friedrich et al., 2012, Viruses, 4(9):1619-50). The EBOV glycoprotein GP is an essential component of a vaccine that protects against exposures with the same species of EBOV. Furthermore, inclusion of the GP from EBOV and SUDV, the two most virulent species of ebolaviruses, can protect monkeys against EBOV and SUDV intramuscular exposures, as well as exposures with the distantly related Bundibugyo (BDBV), Taï Forest ebolavirus (TAFV; formerly known as Ivory Coast or Cote d'Ivoire) species. Likewise, inclusion of the GP from MARV can protect monkeys against intramuscular and aerosol MARV exposures. The development of medical countermeasures for these viruses is a high priority, in particular the development of a PAN-filovirus vaccine—that is one vaccine that protects against all pathogenic filoviruses.

Replication-defective adenovirus vectors (rAd) are powerful inducers of cellular immune responses and have therefore come to serve as useful vectors for gene-based vaccines particularly for lentiviruses and filoviruses, as well as other nonviral pathogens (Shiver et al., 2002, Nature, 415(6869): 331-5; Hill et al., 2010, Hum Vaccin 6(1): 78-83; Sullivan et al., 2000, Nature, 408(6812): 605-9; Sullivan et al., 2003, Nature, 424(6949): 681-4; Sullivan et al., 2006, PLoS Med, 3(6): e177; Radosevic et al., 2007, Infect Immun, 75(8): 4105-15; Santra et al., 2009, Vaccine, 27(42): 5837-45).

Adenovirus-based vaccines have several advantages as human vaccines since they can be produced to high titers under GMP conditions and have proven to be safe and immunogenic in humans (Asmuth et al., 2010, J Infect Dis 201(1): 132-41; Kibuuka et al., 2010, J Infect Dis 201(4): 600-7; Koup et al., 2010, PLoS One 5(2): e9015; Catanzaro et al., 2006, J Infect Dis, 194(12): 1638-49; Harro et al., 2009, Clin Vaccine Immunol, 16(9): 1285-92). While most of the initial vaccine work was conducted using rAd5 due to its significant potency in eliciting broad antibody and CD8+ T cell responses, pre-existing immunity to rAd5 in humans may limit efficacy (Catanzaro et al., 2006, J Infect Dis, 194(12): 1638-49; Cheng et al., 2007, PLoS Pathog, 3(2): e25; McCoy et al., 2007, J Virol, 81(12): 6594-604; Buchbinder et al., 2008, Lancet, 372(9653): 1881-93). This property might restrict the use of rAd5 in clinical applications for many vaccines that are currently in development including Ebolavirus (EBOV) and Marburg virus (MARV).

Replication-defective adenovirus vectors, rAd26 and rAd35, derived from adenovirus serotype 26 and serotype 35, respectively, have the ability to circumvent Ad5 pre-existing immunity. rAd26 can be grown to high titers in Ad5 E1-complementing cell lines suitable for manufacturing these vectors at a large scale and at clinical grade (Abbink, et al., 2007, J Virol, 81(9):4654-63), and this vector has been shown to induce humoral and cell-mediated immune responses in prime-boost vaccine strategies (Abbink, et al., 2007, J Virol, 81(9):4654-63; Liu et al., 2009, Nature, 457(7225): 87-91). rAd35 vectors grow to high titers on cell lines suitable for production of clinical-grade vaccines (Havenga et al., 2006, J Gen Virol, 87: 2135-43), and have been formulated for injection as well as stable inhalable powder (Jin et al., 2010, Vaccine 28(27): 4369-75). These vectors show efficient transduction of human dendritic cells (de Gruijl et al., 2006, J Immunol, 177(4): 2208-15; Lore et al., 2007, J Immunol, 179(3): 1721-9), and thus have the capability to mediate high level antigen delivery and presentation.

Modified Vaccinia Ankara (MVA) virus is related to Vaccinia virus, a member of the genera Orthopoxvirus in the family of Poxviridae. Poxviruses are known to be good inducers of CD8 T cell responses because of their intracytoplasmic expression. However, they may be poor at generating CD4 MHC class II restricted T cells (see for example Haslett et al., 2000, Journal of Infectious Diseases, 181: 1264-72, page 1268). MVA has been engineered for use as a viral vector for recombinant gene expression or as recombinant vaccine.

Strains of MVA having enhanced safety profiles for the development of safer products, such as vaccines or pharmaceuticals, have been developed by Bavarian Nordic. MVA was further passaged by Bavarian Nordic and is designated MVA-BN, a representative sample of which was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein in their entirety.

MVA-BN can attach to and enter human cells where virally-encoded genes are expressed very efficiently. MVA-BN is replication incompetent, meaning that the virus does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), Antivir. Ther. 10(2):285-300; A. Cosma et al. (2003), Vaccine 22(1):21-9; M. Di Nicola et al. (2003), Hum. Gene Ther. 14(14):1347-1360; M. Di Nicola et al. (2004), Clin. Cancer Res., 10(16):5381-5390].

Protective immunity to infection relies on both the innate and adaptive immune response. The adaptive immune response includes production of antibodies by B cells (humoral immune response) and the cytotoxic activity of CD8+ effector T cells (cellular immune response) and CD4+ T cells, also known as helper T cells, who play a key role in both the Immoral and the cellular immune response.

CD4+ T cells are stimulated by antigens to provide signals that promote immune responses. CD4+ T cells act through both cell-cell interactions and the release of cytokines to help trigger B cell activation and antibody production, activation and expansion of cytotoxic CD8+ T cells, and macrophage activity.

Antibody-mediated protection can be extraordinarily long-lived, and neutralizing antibodies present at the time of pathogen encounter can prevent rather than combat infection, thereby achieving 'sterilizing' immunity (Swain et al., 2012, Nat Rev Immunol, 12(2): 136-148). Following viral infection, CD4+ signaling is necessary to direct the formation of germinal centers, where CD4+ cells promote B cell isotype switching and affinity maturation of antibody responses as well as the generation of B cell memory and long-lived antibody-producing plasma cells. Thus, CD4+ cells are likely to be important for generating long-lived antibody responses and protective immunity to most, if not all, pathogens.

The role of CD4+ T cells in helping the priming, effector function, and memory of CD8+ T cells is especially important in the case of chronic infections, when CD8+ T cells rely on continued rounds of expansion, for which CD4+ T cell cytokine production is critical (Swain et al., 2012, Nat Rev Immunol, 12(2): 136-148).

Recent data has indicates that the role of CD4+ T cells extend further than that of cytokine production. For example, CD4+ T cells can recruit key lymphoid populations into secondary lymphoid tissue or sites of pathogen infection (Sant and McMichael, 2012, J Exp Med, 209(8): 1391-5). Specifically, CD4+ T cells can promote engagement of CD8+ T cells with dendritic cells in secondary lymphoid tissue, cause influx of lymphoid cells into draining lymph nodes, and recruit effectors to the site of viral replication. In addition, CD4+ T cells can also protect against pathogens through direct cytolytic activity.

Following the resolution of primary immune responses, or after successful vaccination, most pathogen-specific effector CD4+ T cells die, leaving behind a small population of long-lived memory cells. Memory CD4+ T cells enhance early innate immune responses following infections in the tissues that contribute to pathogen control (Swain et al., 2012, Nat Rev Immunol, 12(2): 136-148). Importantly, CD4+ T cells provide more rapid help to B cells, and potentially to CD8+ T cells, thereby contributing to a faster and more robust immune response.

The range of functions of CD4+ T cells during an immune response highlights their key role in generating highly effective immune protection against pathogens. Recent studies have provided new evidence for CD4+ T cells as direct effectors in antiviral immunity (Sant et al., 2012, *J. Exp. Med.* 209: 1391-1395). Preexisting influenza-specific CD4+ T cells were reported to correlate with disease protection against influenza challenge in humans (Wilkinson et al., 2012, *Nature Medicine,* 18: 274-280).

Several assays are used to detect immune responses, including, e.g., ELISA (enzyme-linked immunosorbent assay), ELISPOT (enzyme-linked immunospot), and ICS (intracellular cytokine staining). ELISA assays analyze, e.g., levels of secreted antibodies or cytokines. When ELISA assays are used to determine levels of antibodies that bind to a particular antigen, an indicator of the humoral immune response, they may also reflect CD4+ T cell activity, as the production of high-affinity antibodies by B cells depends on the activity of CD4+ helper T cells. ELISPOT and ICS are single-cell assays that analyze, e.g., T cell responses to a particular antigen. ELISPOT assays measure the secretory activity of individual cells, and ICS assays analyze levels of intracellular cytokine. CD4+ specific and CD8+ specific T cell responses can be determined using ICS assays.

There are published papers testing methods for using MVA-Ad prime-boost regimens in animals, such as monkeys and mice. However, no MVA-Ad prime-boost regimen has been shown to be more effective at stimulating an immune response than the complementary Ad-MVA prime-boost regimen until now. For example, Barouch et al. (2012, Nature, 482(7383):89-93) found that, in monkeys, a heterologous regimen comprising MVA/M26 was "comparatively less efficacious than Ad26/MVA or Ad35/Ad26, which reduced viral load set-points by greater than 100-fold." In particular, the cellular immune response to SIV Gag, Pol, and Env in rhesus monkeys was less-pronounced for the MVA/Ad26 prime-boost regimen administered on a 0-24 week schedule than for the opposite Ad26/MVA regimen, as measured by IFN-gamma ELISPOT and ICS assays. The antibody response was also less effective for the MVA/Ad26 regimen than for the Ad26/MVA regimen, as evidenced by an ELISA assay, though to a lesser extent. Roshorm et al. (2012, Eur J Immunol, 42(12):3243-55) found that an MVA/ChAdV68 prime-boost regimen administered in mice on a 0-4 week schedule was no more effective at inducing an immune response to HIV Gag than the opposite ChAdV68/MVA regimen, as measured by an ICS assay for CD8+ T cell activity. Gilbert et al. (2002, Vaccine, 20(7-8):1039-45) found that an MVA/Ad5 prime-boost regimen administered in mice on a 0-14 day schedule was slightly less effective in producing an immune response to Plasmodium CS than the opposite Ad5/MVA regimen, as measured by an ELISPOT assay. The MVA/Ad5 regimen was even less effective than the Ad5/MVA regimen when both were administered on a 0-10 day schedule. Additionally, the MVA/Ad5 regimen was less effective in protecting immunized mice against a challenge infection (80% vs. 100% protection). None of these reports indicate that an MVA/Ad regimen can result in a stronger humoral and/or cellular immune response in humans, than an Ad/MVA regimen.

There is an unmet need for improved vaccines that elicit broad and strong immune responses in humans against antigenic proteins, and particularly vaccines that provide protective immunity against the deadly Ebola and Marburg filoviruses.

BRIEF SUMMARY OF THE INVENTION

It is now discovered, for the first time, that a specific order of administration of prime-boost regimens of replication incompetent vectors generates an improved effective immune response that could be applied to provide treatment and/or protection against a disease, such as a tumor or an infectious disease, more particularly an infection by a filovirus, in a human subject. Surprisingly, it has now been found that different from the previously reported animal studies, use of an MVA vector as a prime and an adenovirus vector as a boost generates a superior immune response against an immunogen, characterized by a strong induction of T cell activity and a high level of antibody response specific to the immunogen.

In certain embodiments of the invention, MVA-prime and adenovirus-boost combinations of replication incompetent vectors generate an enhanced immune response to an antigenic protein or an immunogenic polypeptide thereof in a human subject. The antigenic protein or immunogenic polypeptide thereof can be any antigenic protein or immunogenic polypeptide thereof. For example, the antigenic protein or immunogenic polypeptide thereof can be derived from a pathogen, e.g., a virus, a bacterium, a fungus, a protozoan, or a tumor.

Accordingly, one general aspect of the invention relates to a method of enhancing an immune response in a human subject, the method comprising:
  a. administering to the human subject a first composition comprising an immunologically effective amount of a MVA vector comprising a first polynucleotide encoding an antigenic protein or an immunogenic polypeptide thereof for priming the immune response; and
  b. administering to the subject a second composition comprising an immunologically effective amount of an adenovirus vector comprising a second polynucleotide encoding the antigenic protein or an immunogenic polypeptide thereof for boosting the immune response;
  to thereby obtain an enhanced immune response against the antigenic protein in the human subject.

In a preferred embodiment of the invention, the enhanced immune response comprises an enhanced antibody response against the antigenic protein in the human subject.

In a preferred embodiment of the invention, the enhanced immune response comprises an enhanced CD4+ and/or CD8+ T cell response against the antigenic protein in the human subject.

Another aspect of the invention relates to a method of eliciting an immune response in a human subject, the method comprising:
  a. administering to the human subject a first composition comprising an immunologically effective amount of a MVA vector comprising a first polynucleotide encoding an antigenic protein or an immunogenic polypeptide thereof for priming the immune response; and
  b. administering to the subject a second composition comprising an immunologically effective amount of an adenovirus vector comprising a second polynucleotide encoding the antigenic protein or an immunogenic polypeptide thereof for boosting the immune response;
  to thereby obtain an enhanced immune response in the human subject relative to the immune response that would be observed if the second composition would be administered for priming and the first composition would be administered for boosting the immune response.

In a preferred embodiment of the invention, the enhanced immune response generated by the method comprises an enhanced antibody response against the antigenic protein in the human subject. Such a response can e.g. be characterized by the presence of a high proportion of responders, such as more than 50%, 60%, 70%, 80%, 90%, or 100% of subjects tested.

In one embodiment of the invention, the enhanced immune response generated by the method comprises an enhanced CD8+ T cell response against the antigenic protein in the human subject [e.g. a response characterized by the presence of a high proportion of CD8+ responders, such as more than 50%, 60%, 70%, 80%, 90%, or 100% of subjects tested as determined by an ICS assay, with a median total cytokine response of about 0.1%, 0.2%, 0.3%, 0.4%, 0.5% or more]. In another embodiment of the invention, the enhanced CD8+ T cell response generated by the method comprises an increase or induction of poly functional CD8+ T cells specific to the antigenic protein. Such polyfunctional CD8+ T cells express more than one cytokine, such as two or more of IFN-gamma, IL-2 and TNF-alpha.

In one embodiment of the invention, the enhanced immune response generated by the method comprises an enhanced CD4+ T cell response against the antigenic protein in the human subject [e.g. a response characterized by the presence of a high proportion of CD4+ responders, such as more than 50%, 60%, 70%, 80%, 90%, or 100% of subjects tested as determined by an ICS assay, with a median total cytokine response of about 0.1%, 0.2%, 0.3%, 0.4%, 0.5% or more]. In another embodiment of the invention, the enhanced CD4+ T cell response generated by the method comprises an increase or induction of polyfunctional CD4+ T cells specific to the antigenic protein. Such polyfunctional CD4+ T cells express more than one cytokine, such as two or more of IFN-gamma, IL-2 and TN F-alpha.

In another preferred embodiment of the invention, the enhanced immune response further comprises an enhanced antibody response against the antigenic protein in the human subject. Such a response can e.g. be characterized by the presence of a high proportion of responders, such as more than 50%, 60%, 70%, 80%, 90%, or 100% of subjects tested. In another embodiment of the invention, the enhanced immune response further comprises an enhanced CD8+ T cell response against the antigenic protein in the human subject [e.g. a response characterized by the presence of a high proportion of CD8+ responders, such as more than 50%, 60%, 70%, 80%, 90%, or 100% of subjects tested as determined by an ICS assay, with a median total cytokine response of about 0.1%, 0.2%, 0.3%, 0.4%, 0.5% or more]. In one embodiment of the invention, the enhanced CD8+ T cell response generated by the method comprises an increase or induction of polyfunctional CD8+ T cells specific to the antigenic protein in the human subject.

In a more preferred embodiment of the invention, the enhanced immune response comprises an enhanced CD4+ T cell response, an enhanced antibody response and an enhanced CD8+ T cell response, against the antigenic protein in the human subject.

In a preferred embodiment of the invention, the adenovirus vector is a rAd26 vector.

In another preferred embodiment of the invention, the boosting step (b) is conducted 1-12 weeks after the priming step (a). In yet another embodiment of the invention, the boosting step (b) is repeated one or more times after the initial boosting step.

In a preferred embodiment of the invention, the boosting step (b) is conducted 2-12 weeks after the priming step (a). In another preferred embodiment of the invention, the boosting step (b) is conducted 4-12 weeks after the priming step (a). In another preferred embodiment of the invention, the boosting step (b) is conducted 1 week after the priming step (a). In another preferred embodiment of the invention, the boosting step (b) is conducted 2 weeks after the priming step (a). In another preferred embodiment of the invention, the boosting step (b) is conducted 4 weeks after the priming step (a). In another preferred embodiment of the invention, the boosting step (b) is conducted 8 weeks after the priming step (a).

In an embodiment of the invention, the antigenic protein is derived from a pathogen, such as a virus, a bacterium, a fungus, or a protozoan. In another embodiment of the invention, the antigenic protein is derived from a tumor, preferably a cancer.

In an embodiment of the invention, the first polynucleotide and the second polynucleotide encode for the same antigenic protein or immunogenic polypeptide thereof. In another embodiment of the invention, the first polynucleotide and the second polynucleotide encode for different immunogenic polypeptides or epitopes of the same antigenic protein. In yet another embodiment of the invention, the first polynucleotide and the second polynucleotide encode for different, but related, antigenic proteins or immunogenic polypeptide thereof. For example, the related antigenic proteins can be substantially similar proteins derived from the same antigenic protein, or different antigenic proteins derived from the same pathogen or tumor.

According to embodiment of the invention, a method of the invention provides a protective immunity to the human subject against a disease associated with the antigenic protein, such as a tumor or an infectious disease.

In one preferred embodiment, the prime-boost combination of replication incompetent MVA and adenovirus vectors enhances a protective immune response against a tumor in a human subject.

In another preferred embodiment, the prime-boost combination of replication incompetent MVA and adenovirus vectors enhances an immune response against a pathogen, more preferably one or more filovirus subtypes, such as the Ebola and/or Marburg filoviruses, in a human subject.

The filovirus subtypes according to the invention can be any filovirus subtype. In a preferred embodiment, the filovirus subtypes are selected from the group of Zaire, Sudan, Reston, Bundibugyo, Taï Forest and Marburg. The antigenic proteins can be any protein from any filovirus comprising an antigenic determinant. In a preferred embodiment the antigenic proteins are glycoproteins or nucleoproteins. The antigenic proteins encoded by the MVA vectors or adenovirus vectors comprised in the first and second composition according to the invention can be any antigenic protein from any filovirus.

In another preferred embodiment, the MVA vector in the first composition comprises a nucleic acid encoding antigenic proteins of at least four filovirus subtypes. Preferably, the MVA vector comprises a nucleic acid encoding one or more antigenic proteins having the amino acid sequences of SEQ ID NO: 1, SEQ ID NO: 2, SEQ ID NO: 4, and SEQ ID NO: 5. Most preferably, the MVA vector comprises a nucleic acid encoding four antigenic proteins having the amino acid sequences of SEQ ID NO: 1, SEQ ID NO: 2, SEQ ID NO: 4, and SEQ ID NO: 5.

In certain embodiments, the second composition comprises at least one adenovirus vector comprising a nucleic acid encoding an antigenic protein of at least one filovirus subtype. The at least one filovirus subtype encoded by the adenovirus can be selected from any of the four filovirus subtypes encoded by the MVA vector, or a new subtype not encoded by the MVA vector. In a preferred embodiment, the antigenic protein of the at least one filovirus subtype encoded by the adenovirus vector has the amino acid sequence selected from the group consisting of SEQ ID NO:1, SEQ ID NO:2, SEQ ID NO:3, SEQ ID NO:4, and SEQ ID NO:5.

In another embodiment, the second composition comprises more than one adenovirus vectors, each comprising a nucleic acid encoding an antigenic protein of at least one filovirus subtype. The antigenic proteins encoded by the more than one adenovirus vectors can be the same or different antigenic proteins. For example, the second composition can comprise a first adenovirus vector comprising a nucleic acid encoding a first antigenic protein having an amino acid sequence selected from the group consisting of SEQ ID NO:1, SEQ ID NO:2, SEQ ID NO:3, SEQ ID NO:4, and SEQ ID NO:5. The second composition can further comprise a second adenovirus vector comprising a nucleic acid encoding a second antigenic protein having an amino acid sequence selected from the group consisting of SEQ ID NO:1, SEQ ID NO:2, SEQ ID NO:3, SEQ ID NO:4, and SEQ ID NO:5. The second composition can additionally comprise a third adenovirus vector comprising a nucleic acid encoding a third antigenic protein having an amino acid sequence selected from the group consisting of SEQ ID NO:1, SEQ ID NO:2, SEQ ID NO:3, SEQ ID NO:4, and SEQ ID NO:5. The first, second and third adenovirus vectors can be same or different. The first, second and third antigenic proteins can be same or different.

In a preferred embodiment, the second composition comprises a first adenovirus vector comprising a nucleic acid encoding an antigenic protein having the amino acid sequence of SEQ ID NO:1. In another embodiment, the second composition further comprises a second adenovirus vector comprising a nucleic acid encoding an antigenic protein having the amino acid sequence of SEQ ID NO:2. In yet another embodiment, the second composition additional comprises a third adenovirus vector comprising a nucleic acid encoding an antigenic protein having the amino acid sequence of SEQ ID NO:3.

It is contemplated that the methods, vaccines, and compositions described herein can be embodied in a kit. For example, in one embodiment, the invention can include a kit comprising:

(a) a first composition comprising an immunologically effective amount of a MVA vector comprising a nucleic acid encoding an antigenic protein of a first filovirus subtype or a substantially similar antigenic protein, together with a pharmaceutically acceptable carrier; and (b) a second composition comprising an immunologically effective amount of an adenovirus vector comprising a nucleic acid encoding antigenic proteins of at least one filovirus subtype or a substantially similar antigenic protein, together with a pharmaceutically acceptable carrier;

wherein composition (a) is a priming composition and composition (b) is a boosting composition.

In a preferred embodiment, the invention relates to a combination vaccine, a kit or a use wherein the MVA vector in the first composition comprises a nucleic acid encoding one or more antigenic proteins from four different filovirus subtypes having the amino acid sequences of SEQ ID NO: 1, SEQ ID NO: 2, SEQ ID NO: 4, and SEQ ID NO: 5, preferably all four of the antigenic proteins; and wherein the adenovirus vector in the second composition comprises a nucleic acid encoding an antigenic protein having the amino acid sequence of SEQ ID NO: 1.

In yet another preferred embodiment, the invention relates to a combination vaccine, a kit or a use wherein the MVA vector in composition (a) comprises a nucleic acid encoding one or more antigenic proteins from four different filovirus subtypes having SEQ ID NO: 1, SEQ ID NO: 2, SEQ ID NO: 4, and SEQ ID NO: 5, preferably all four of the antigenic proteins; and wherein the second composition comprises at least one adenovirus comprising a nucleic acid encoding an antigenic protein with SEQ ID NO: 1, at least one adenovirus comprising a nucleic acid encoding an antigenic protein with SEQ ID NO: 2, and at least one adenovirus comprising a nucleic acid encoding an antigenic protein with SEQ ID NO: 3.

In a preferred embodiment, the adenovirus vectors comprised in the combination vaccine or kit of the invention or the adenovirus vectors used for generating a protective immune response against at least one of the filovirus subtypes, are rAd26 or rAd35 vectors.

In another preferred embodiment, the priming vaccination is conducted at week 0, followed by a boosting vaccination at week 1, 2, 3, 4, 5, 6, 7, 8, 9, 10, 11, 12, or later. Preferably, the boosting vaccination is administered at week 1-10, more preferably at week 1, 2, 4 or 8.

According to embodiments of the invention, the boosting step (b) can be repeated one or more times after the initial boosting step. The additional boosting administration can be performed, for example, 6 months, 1 year, 1.5 years, 2 years, 2.5 years, 3 years after the priming administration, or later.

In a preferred embodiment of the invention, the method comprises a priming vaccination with an immunologically effective amount of one or more MVA vectors expressing one or more filovirus glycoproteins, followed by a boosting vaccination with an immunologically effective amount of one or more adenovirus vectors, preferably Ad26 vectors expressing one or more filovirus glycoproteins or substantially similar glycoproteins.

In preferred embodiments of the invention, the one or more filoviruses are Ebolaviruses or Marburg viruses. The Ebolavirus can be of any species, for example, Zaire ebolavirus (EBOV) and Sudan ebolavirus (SUDV), Reston, Bundibugyo, Taï Forest. The Marburg virus (MARV) can be of any species. Exemplary amino acid sequences of suitable filovirus antigenic proteins are shown in SEQ ID NO: 1 to SEQ ID NO: 5.

The invention also relates to use of the first and second compositions according to embodiments of the invention for enhancing an immune response in a human subject, wherein the first composition is administered to the human subject for priming the immune response, and the second composition is administered to the human subject for boosting the immune response, to thereby obtain an enhanced immune response against the antigenic protein in the human subject.

The invention further relates to:
a. a first composition comprising an immunologically effective amount of a MVA vector comprising a first polynucleotide encoding an antigenic protein or an immunogenic polypeptide thereof; and
b. a second composition comprising an immunologically effective amount of an adenovirus vector comprising a second polynucleotide encoding the antigenic protein or an immunogenic polypeptide thereof for boosting the immune response;
the first and second compositions for use in inducing an enhanced immune response against the antigenic protein in a human subject, wherein the first composition is administered to the human subject for priming the immune response, and the second composition is administered to the human subject one or more times for boosting the immune response.

In one preferred embodiment, the antigenic protein or an immunogenic polypeptide thereof encoded by the first polynucleotide is derived from a pathogen or a tumor. In another preferred embodiment, the antigenic protein or an immunogenic polypeptide thereof encoded by the first polynucleotide is derived from a filovirus. In yet another embodiment, the antigenic proteins comprise the amino acid sequences selected from the group of SEQ ID NO: 1, SEQ ID NO: 2, SEQ ID NO: 3, SEQ ID NO: 4, and SEQ ID NO: 5. Most preferably, the MVA vector comprises a polynucleotide encoding the antigenic proteins having the amino acid sequences of SEQ ID NO: 1, SEQ ID NO: 2, SEQ ID NO: 4, and SEQ ID NO: 5.

More preferably, the adenovirus vector comprises a polynucleotide encoding at least one antigenic protein having the amino acid sequence of SEQ ID NO: 1, SEQ ID NO: 2, SEQ ID NO: 3. In a more preferred embodiment, the adenovirus vector comprises a polynucleotide encoding the antigenic protein having the amino acid sequence of SEQ ID NO: 1. Preferably said adenovirus vector is an rAd26 vector.

The invention further relates to:
a. a first composition comprising an immunologically effective amount of a MVA vector comprising a first polynucleotide encoding an antigenic protein or an immunogenic polypeptide thereof; and
b. a second composition comprising an immunologically effective amount of an adenovirus vector comprising a second polynucleotide encoding the antigenic protein or an immunogenic polypeptide thereof for boosting the immune response;
wherein the first composition is administered to a human subject for priming the immune response, and the second composition is administered to the human subject for boosting the immune response, for use in inducing an enhanced humoral and/or cellular immune response in the human subject relative to the humoral and/or cellular immune response that would be observed if the second composition would be administered for priming and the first composition would be administered for boosting the immune response.

In one embodiment of the invention, the enhanced immune response generated by said compositions a. and b. comprises an increase of the antibody response against the antigenic protein in the human subject combined with a CD4+ and CD8+ response [e.g., a response characterized by the presence of a high proportion of CD4+ and CD8+ responders, such as more than 50%, 60%, 70%, 80%, 90% or 100% of subjects tested as determined by an ICS assay, with a median total cytokine response of about 0.2%, 0.3%, 0.4%, 0.5% or more]. In another embodiment of the invention, the enhanced CD4+ and CD8+ T cell responses generated by said compositions a. and b. comprises an increase or induction of polyfunctional CD4+ and CD8+ T cells specific to the antigenic protein. Such polyfunctional CD4+ T cells express more than one cytokine, such as two or more of IFN-gamma, IL-2 and TNF-alpha.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. It should be understood that the invention is not limited to the precise embodiments shown in the drawings.

In the drawings:

Figure 2:
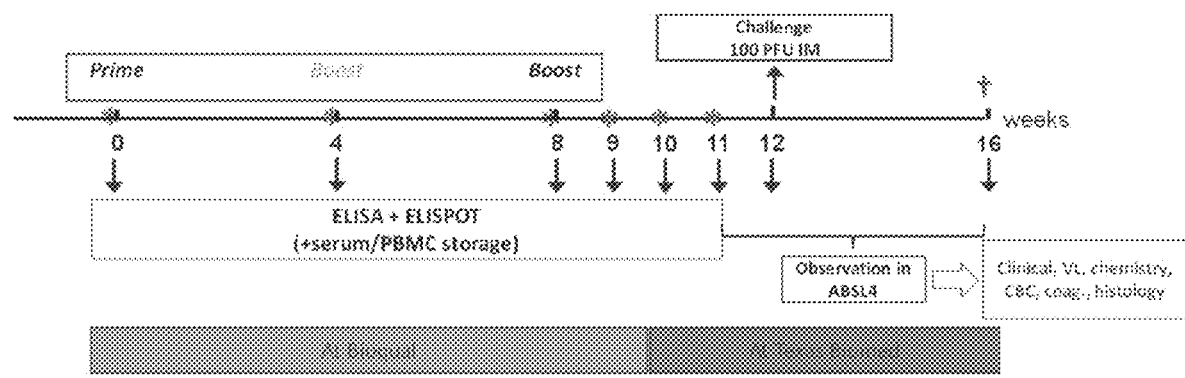
Figure 3:
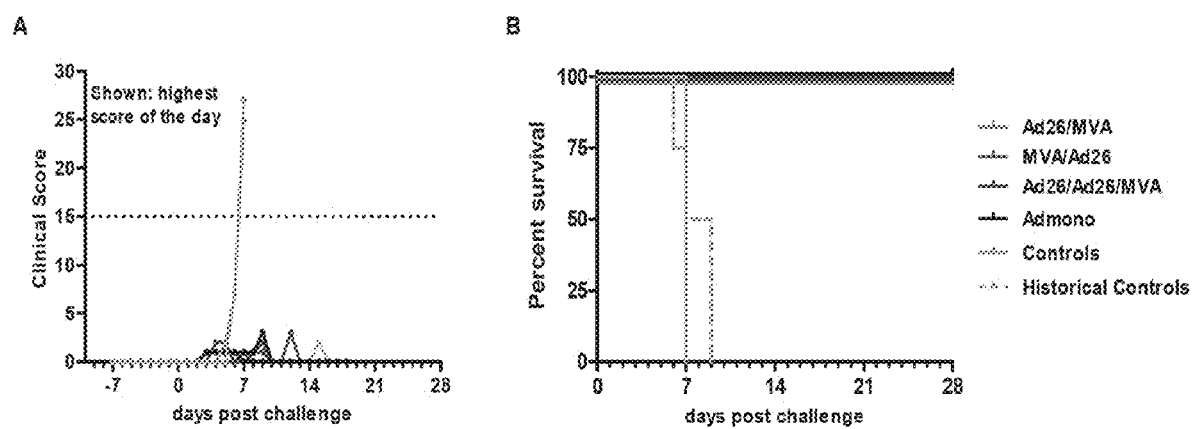
Figure 4:
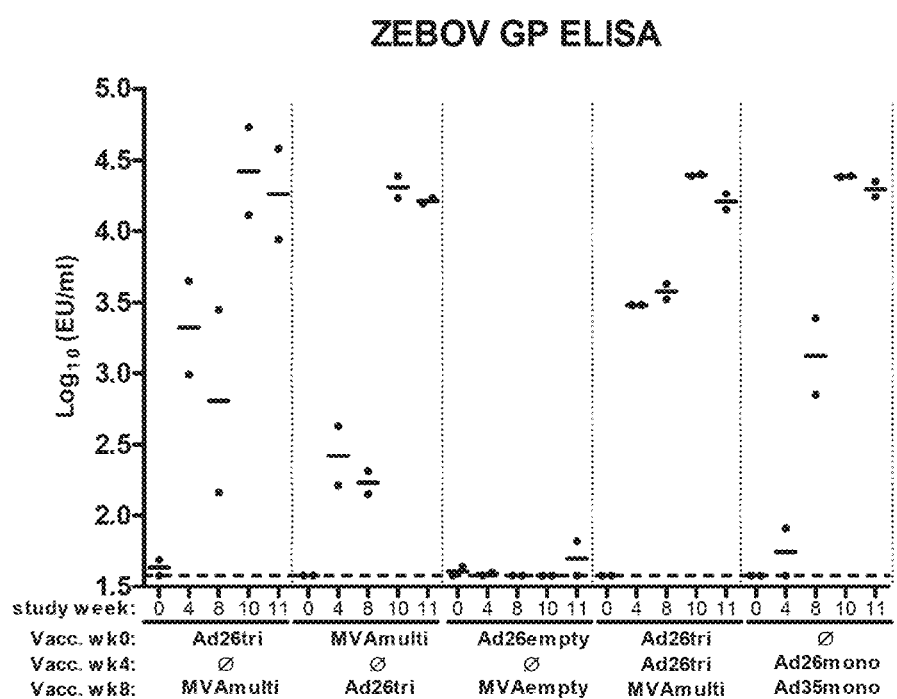

FIG. 1 summarizes the grouping in an animal study;

FIG. 2 illustrates the experimental design of the study;

FIG. 3 shows the outcome of challenge with the challenge strain Ebola Zaire Kikwit 1995;

FIG. 4 shows the Ebola Zaire glycoprotein specific humoral immune response (assessed by ELISA) observed from the animal study: very high antibody titers were obtained independently of the vaccination regimes (ND=time-point not analyzed);

Figure 5:
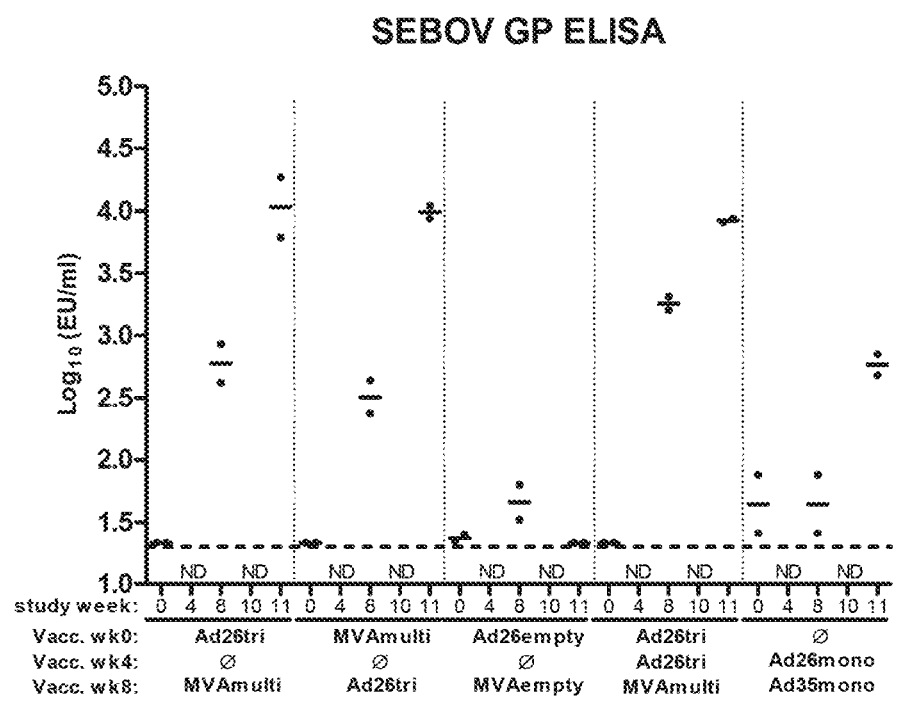

FIG. 5 shows the Sudan Gulu glycoprotein specific humoral immune response (assessed by ELISA) observed from the animal study: very high antibody titers were obtained independently of the vaccination regimes (ND=time-point not analyzed);

FIG. 6 shows the Marburg Angola glycoprotein specific humoral immune response (assessed by ELISA) observed from the animal study: very high antibody titers were obtained independently of the vaccination regimes (ND=time-point not analyzed);

FIG. 7 shows the specific cellular immune response to ZEBOV, SEBOV and MARVA GP analyzed by an IFN-γ ELISPOT;

FIG. 8 shows the specific immune response to ZEBOV GP analyzed by an anti-EBOV GP ELISA, wherein at 21 days post boost immunization, a higher humoral immune response post boost immunization is observed in subjects immunized with MVA as a prime and Ad26 as a boost than with the reverse order of vaccines;

FIG. 9 shows the specific T cell response to ZEBOV GP in humans analyzed by ELISpot assay;

FIG. 10 shows the specific CD8+ cellular immune response to ZEBOV GP in humans analyzed by ICS assay;

FIG. 11 shows the functionality of the EBOV GP-specific CD8+ T cell responses in humans by ICS assay when using a 28 days prime boost interval;

FIG. 12 shows the functionality of the EBOV GP-specific CD8+ T cell responses in humans by ICS assay when using a 56 days prime boost interval;

FIG. 13 shows the specific CD4+ cellular immune response to ZEBOV GP in humans analyzed by ICS assay; and FIG. 14 shows the functionality of the EBOV GP-specific CD4+ T cell responses in humans by ICS assay when using a 28 days prime boost interval;

FIG. 15 shows the functionality of the EBOV GP-specific CD4+ T cell responses in humans by ICS assay when using a 56 days prime boost interval;

FIG. 16 shows the immune response induced by a prime immunization with Ad26.ZEBOV followed by a MVA-BN-Filo boost 14 days later assessed by ELISA (A), ELIspot (B), and ICS (C and D);

FIG. 17 shows the specific immune response to ZEBOV GP analyzed by an anti-EBOV GP ELISA;

FIG. 18 shows the specific T cell response to ZEBOV GP in humans analyzed by ELISpot assay;

FIG. 19 shows the strong and balanced CD4+ (A) and CD8+ (B) cellular immune response specific to ZEBOV GP in humans analyzed by ICS assay and the functionality of the EBOV GP-specific CD8+ (C) and CD4+ (D) T cell responses in humans by ICS assay when using MVA as a prime and Ad26 as a boost 14 days later.

FIG. 20 shows EBOV Mayinga GP-binding Antibodies Elicited by Vaccination With Ad26.ZEBOV/MVA-BN-Filo and MVA-BN-Filo/Ad26.ZEBOV Regimens Determined by GP ELISA. Vaccination regimens are indicated below x-axis. High IM and standard IM refer to dose and route of MVA BN Filo. Horizontal dotted line indicates LOD.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, the term "protective immunity" or "protective immune response" means that the vaccinated subject is able to control an infection or a disease related to an antigenic protein or immunogenic polypeptide thereof against which the vaccination was done. Usually, the subject having developed a "protective immune response" develops only mild to moderate clinical symptoms or no symptoms at all. Usually, a subject having a "protective immune response" or "protective immunity" against a certain antigenic protein will not die as a result of an infection or disease related to the antigenic protein.

The antigenic protein can be a native protein from a pathogen or a tumor, or a modified protein based on a native protein from a pathogen or a tumor.

As used herein, the term "pathogen" refers to an infectious agent such as a virus, a bacterium, a fungus, a parasite, or a prion that causes disease in its host.

As used herein, the term "enhanced" when used with respect to an immune response, such as a CD4+ T cell response, an antibody response, or a CD8+ T cell response, refers to an increase in the immune response in a human subject administered with a prime-boost combination of replication incompetent MVA and adenovirus vectors according to the invention, relative to the corresponding immune response observed from the human subject administered with a reverse prime-boost combination, wherein the adenovirus vector is provided as a prime and the MVA vector is provided to boost the immune response, using the same prime-boost interval.

As used herein, the term "dominant CD4+ or CD8+ T cell response" refers to a T cell immune response that is characterized by observing high proportion of immunogen-specific CD4+ T cells within the population of total responding T cells following vaccination. The total immunogen-specific T-cell response can be determined by an IFN-gamma ELISPOT assay. The immunogen-specific CD4+ or CD8+ T cell immune response can be determined by an ICS assay. For example, a dominant CD4+ T cell response can comprise an antigen specific CD4+ T cell response that is more than 50%, such as 51%, 60%, 70%, 80%, 90% or 100% of the total antigen specific T-cell responses in the human subject. Preferably, the dominant CD4+ T cell response also represents 0.1% or more, such as 0.1%, 0.2%, 0.3%, 0.4%, 0.5%, or more of the total cytokine responses in the human subject.

As used herein, the term "enhanced antibody response" refers to an antibody response in a human subject administered with a prime-boost combination of replication incompetent MVA and adenovirus vectors according to the invention, that is increased by a factor of at least 1.5, 2, 2.5, or more relative to the corresponding immune response observed from the human subject administered with a reverse prime-boost combination, wherein the adenovirus vector is provided as a prime and the MVA vector is provided to boost the immune response, using the same prime-boost interval.

As used herein, the term "polyfunctional" when used with respect to CD4+ or CD8+ T cells means T cells that express more than one cytokine, such as at least two of: IL-2, IFN-gamma, and TNF-alpha.

An "adenovirus capsid protein" refers to a protein on the capsid of an adenovirus (e.g., Ad 26 or Ad 35) that is involved in determining the serotype and/or tropism of a particular adenovirus. Adenoviral capsid proteins typically include the fiber, penton and/or hexon proteins. As used herein a "Ad26 capsid protein" or a "Ad35 capsid protein" can be, for example, a chimeric capsid protein that includes at least a part of an Ad26 or Ad35 capsid protein. In certain embodiments, the capsid protein is an entire capsid protein of Ad26 or of Ad35. In certain embodiments, the hexon, penton and fiber are of Ad26 or of Ad35.

The terms "adjuvant" and "immune stimulant" are used interchangeably herein, and are defined as one or more substances that cause stimulation of the immune system. In this context, an adjuvant is used to enhance an immune response to the adenovirus and/or MVA vectors of the invention.

The term "corresponding to", when applied to positions of amino acid residues in sequences, means corresponding positions in a plurality of sequences when the sequences are optimally aligned.

The terms "identical" or percent "identity," in the context of two or more nucleic acids or polypeptide sequences, (e.g., glycoproteins of filovirus and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "substantially similar" in the context of the filovirus antigenic proteins of the invention indicates that a polypeptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

It is discovered in the invention that heterologous prime-boost combinations, in particular, MVA priming followed by Ad26 boosting, are surprisingly effective in generating protective immune responses in human subjects.

Antigenic Proteins

Any DNA of interest can be inserted into the viral vectors described herein to be expressed heterologously from the vectors. Foreign genes for insertion into the genome of a virus in expressible form can be obtained using conventional techniques for isolating a desired gene. For organisms which contain a DNA genome, the genes encoding an antigen of interest can be isolated from the genomic DNA; for organisms with RNA genomes, the desired gene can be isolated from cDNA copies of the genome. The antigenic protein can also be encoded by a recombinant DNA that is modified based on a naturally occurring sequence, e.g., to optimize the antigenic response, gene expression, etc.

In certain embodiments of the invention, MVA-prime and adenovirus-boost combinations of replication incompetent vectors generate an enhanced immune response to an antigenic protein or an immunogenic polypeptide thereof in a human subject. The antigenic protein can be any antigenic protein related to an infection or disease.

According to embodiments of the invention, the antigenic protein or immunogenic polypeptide thereof can be isolated from, or derived from, a pathogen, such as a virus (e.g., Filovirus, adenovirus, arbovirus, astrovirus, coronavirus, coxsackie virus, cytomegalovirus, Dengue virus, Epstein-Barr virus, hepatitis virus, herpesvirus, human immunodeficiency virus, human papilloma virus, human T-lymphotropic virus, influenza virus, JC virus, lymphocytic choriomeningitis virus, measles virus, molluscum contagiosum virus, mumps virus, norovirus, parovirus, poliovirus, rabies virus, respiratory syncytial virus, rhinovirus, rotavirus, rotavirus, rubella virus, smallpox virus, varicella zoster virus, West Nile virus, etc.), a bacteria (e.g., *Campylobacter jejuni, Escherichia coli, Helicobacter pylori, Mycobacterium tuberculosis, Neisseria gonorrhoeae, Neisseria meningitides, Salmonella, Shigella, Staphylococcus aureus, Streptococcus*, etc.), a fungus (e.g., Coccidioides immitis, Blastomyces dermatitidis, Cryptococcus neoformans, *Candida* species, *Aspergillus* species, etc.), a protozoan (e.g., Plasmodium, Leishmania, Trypanosome, cryptosporidiums, isospora, Naegleria fowleri, Acanthamoeba, Balamuthia mandrillaris, Toxoplasma gondii, Pneumocystis carinii, etc.), or a cancer (e.g., bladder cancer, breast cancer, colon and rectal cancer, endometrial cancer, kidney cancer, leukemia, lung cancer, melanoma, non-Hodgkin lymphoma, pancreatic cancer, prostate cancer, thyroid cancer, etc.).

In some embodiments, nucleic acids express antigenic domains rather than the entire antigenic protein. These fragments can be of any length sufficient to be immunogenic or antigenic. Fragments can be at least four amino acids long, preferably 8-20 amino acids, but can be longer, such as, e.g., 100, 200, 660, 800, 1000, 1200, 1600, 2000 amino acids long or more, or any length in between.

In some embodiments, at least one nucleic acid fragment encoding an antigenic protein or immunogenic polypeptide thereof is inserted into a viral vector. In another embodiment, about 2-8 different nucleic acids encoding different antigenic proteins are inserted into one or more of the viral vectors. In some embodiments, multiple immunogenic fragments or subunits of various proteins can be used. For example, several different epitopes from different sites of a single protein or from different proteins of the same species, or from a protein ortholog from different species can be expressed from the vectors.

Filovirus Antigenic Proteins

The Ebola viruses, and the genetically-related Marburg virus, are filoviruses associated with outbreaks of highly lethal hemorrhagic fever in humans and primates in North America, Europe, and Africa (Peters, C. J. et al. in: Fields Virology, eds. Fields, B. N. et al. 1161-1176, Philadelphia, Lippincott-Raven, 1996; Peters, C. J. et al. 1994 Semin Virol 5:147-154). Although several subtypes have been defined, the genetic organization of these viruses is similar, each containing seven linearly arrayed genes. Among the viral proteins, the envelope glycoprotein exists in two alternative forms, a 50-70 kilodalton (kDa) secreted protein (sGP) and a 130 kDa transmembrane glycoprotein (GP) generated by RNA editing that mediates viral entry (Peters, C. J. et al. in: Fields Virology, eds. Fields, B. N. et al. 1161-1176, Philadelphia, Lippincott-Raven, 1996; Sanchez, A. et al. 1996 PNAS USA 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: Fields Virology, eds. Fields, B. N. et al. 1161-1176, Philadelphia, Lippincott-Raven, 1996).

The nucleic acid molecules comprised in the adenovirus and MVA vectors may encode structural gene products of any filovirus species, such as subtypes of Zaire (type species, also referred to herein as ZEBOV), Sudan (also referred to herein as SEBOV), Reston, Bundibugyo, and Ivory Coast. There is a single species of Marburg virus (also referred to herein as MARV).

The adenoviral vectors and MVA vectors of the invention can be used to express antigenic proteins which are proteins comprising an antigenic determinant of a wide variety of filovirus antigens. In a typical and preferred embodiment, the vectors of the invention include nucleic acid encoding the transmembrane form of the viral glycoprotein (GP). In other embodiments, the vectors of the invention may encode the secreted form of the viral glycoprotein (ssGP), or the viral nucleoprotein (NP).

One of skill will recognize that the nucleic acid molecules encoding the filovirus antigenic protein can be modified, e.g., the nucleic acid molecules set forth herein can be mutated, as long as the modified expressed protein elicits an immune response against a pathogen or disease. Thus, as used herein, the term "antigenic protein" or "filovirus protein" refers to a protein that comprises at least one antigenic determinant of a filovirus protein described above. The term encompasses filovirus glycoproteins (i.e., gene products of a filovirus) or filovirus nucleoprotein as well as recombinant proteins that comprise one or more filovirus glycoprotein determinants. The term antigenic proteins also encompasses antigenic proteins that are substantially similar.

In some embodiments, the protein can be mutated so that it is less toxic to cells (see e.g., WO/2006/037038) or can be expressed with increased or decreased level in the cells. The invention also includes vaccines comprising a combination of nucleic acid molecules. For example, and without limitation, nucleic acid molecules encoding GP, ssGP and NP of the Zaire, Sudan, Marburg and Ivory Coast/Taï Forest Ebola strains can be combined in any combination, in one vaccine composition.

Adenoviruses

An adenovirus according to the invention belongs to the family of the Adenoviridae and preferably is one that belongs to the genus *Mastadenovirus*. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26 or 35.

An advantage of these serotypes is a low seroprevalence and/or low pre-existing neutralizing antibody titers in the human population. Preparation of rAd26 vectors is described, for example, in WO 2007/104792 and in Abbink et al., (2007) Virol 81(9): 4654-63, both of which are incorporated by reference herein in their entirety. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) J Virol 77(15): 8263-71, all of which are incorporated by reference herein in their entirety. Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al, 2001, J Virol 75: 11603-13; Cohen et al, 2002, J Gen Virol 83: 151-55; Kobinger et al, 2006, Virology 346: 394-401; Tatsis et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Adenoviral Vectors rAd26 and rAd35

In a preferred embodiment according to the invention the adenoviral vectors comprise capsid proteins from two rare serotypes: Ad26 and Ad35. In the typical embodiment, the vector is an rAd26 or rAd35 virus.

Thus, the vectors that can be used in the invention comprise an Ad26 or Ad35 capsid protein (e.g., a fiber, penton or hexon protein). One of skill will recognize that it is not necessary that an entire Ad26 or Ad35 capsid protein be used in the vectors of the invention. Thus, chimeric capsid proteins that include at least a part of an Ad26 or Ad35 capsid protein can be used in the vectors of the invention. The vectors of the invention may also comprise capsid proteins in which the fiber, penton, and hexon proteins are each derived from a different serotype, so long as at least one capsid protein is derived from Ad26 or Ad35. In preferred embodiments, the fiber, penton and hexon proteins are each derived from Ad26 or each from Ad35.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of the Ad26 and Ad35 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad35 or from Ad26 (i.e., the vector is rAd35 or rAd26). In some embodiments, the adenovirus is replication deficient, e.g. because it contains a deletion in the E1 region of the genome. For the adenoviruses of the invention, being derived from Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga et al, 2006, J Gen Virol 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032).

The preparation of recombinant adenoviral vectors is well known in the art.

Preparation of rAd26 vectors is described, for example, in WO 2007/104792 and in Abbink et al., (2007) Virol 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) J Virol 77(15): 8263-71. An exemplary genome sequence of Ad35 is found in GenBank Accession AC_000019.

In an embodiment of the invention, the vectors useful for the invention include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell.

Suitable cell lines include, for example, PER.C6, 911, 293, and E1 A549.

In some embodiments, the Adenovirus virus may express genes or portions of genes that encode antigenic peptides. These foreign, heterologous or exogenous peptides or polypeptides can include sequences that are immunogenic such as, for example, tumor-specific antigens (TSAs), bacterial, viral, fungal, and protozoal antigens.

As noted above, a wide variety of filovirus glycoproteins can be expressed in the vectors. If required, the heterologous gene encoding the filovirus glycoproteins can be codon-optimized to ensure proper expression in the treated host (e.g., human). Codon-optimization is a technology widely applied in the art. Typically, the heterologous gene is cloned into the E1 and/or the E3 region of the adenoviral genome.

The heterologous filovirus gene can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

In a preferred embodiment of the invention, the adenovirus vectors useful for the invention can comprise a wide variety of filovirus glycoproteins known to those of skill in the art. In a further preferred embodiment of the invention, the rAd vector(s) comprises one or more GPs selected from the group consisting of GPs of Zaire ebolavirus (EBOV), GPs of Sudan ebolavirus (SUDV), GPs of Marburg virus (MARV), and GPs substantially similar thereto.

MVA Vectors

MVA vectors useful for the invention utilize attenuated virus derived from Modified Vaccinia Ankara virus which is characterized by the loss of their capabilities to reproductively replicate in human cell lines.

In some embodiments, the MVA virus may express genes or portions of genes that encode antigenic peptides. These foreign, heterologous or exogenous peptides or polypeptides can include sequences that are immunogenic such as, for example, tumor-specific antigens (TSAs), bacterial, viral, fungal, and protozoal antigens.

In other embodiments, the MVA vectors express a wide variety of filovirus glycoproteins as well as other structural filovirus proteins, such as VP40 and nucleoprotein (NP). In one aspect, the invention provides a recombinant modified vaccinia virus Ankara (MVA) comprising a nucleotide sequence encoding an antigenic determinant of a filovirus glycoprotein (GP), in particular an envelope glycoprotein. In another aspect, the invention provides a recombinant MVA vector comprising a heterologous nucleotide sequence encoding an antigenic determinant of a Filovirus glycoprotein, in particular an envelope glycoprotein, and a heterologous nucleotide sequence encoding an antigenic determinant of a further Filovirus protein.

MVA has been generated by more than 570 serial passages on chicken embryo fibroblasts of the dermal vaccinia strain Ankara [Chorioallantois vaccinia virus Ankara virus, CVA; for review see Mayr et al. (1975), Infection 3, 6-14] that was maintained in the Vaccination Institute, Ankara, Turkey for many years and used as the basis for vaccination of humans.

However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [Mayr et al. (1975)]. It was shown in a variety of animal models that the resulting MVA was avirulent [Mayr, A. & Danner, K. (1978), Dev. Biol. Stand. 41: 225-234]. As part of the early development of MVA as a pre-smallpox vaccine, there were clinical trials using MVA-517 in combination with Lister Elstree [Stickl (1974), Prev. Med. 3: 97-101; Stickl and Hochstein-Mintzel (1971), Munch. Med. Wochenschr. 113: 1149-1153] in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), Zentralbl. Bacteriol. (B) 167: 375-390). MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 15% (31 kb from six regions) of the genome compared with ancestral CVA virus. The deletions affect a number of virulence and host range genes, as well as the gene for Type A inclusion bodies. MVA-575 was deposited on Dec. 7, 2000, at the European Collection of Animal Cell Cultures (ECACC) under Accession No. V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells [Blanchard et al. (1998), J. Gen. Virol. 79:1159-1167; Carroll & Moss (1997), Virology 238:198-211; U.S. Pat. No. 5,185,146; Ambrosini et al. (1999), J. Neurosci. Res. 55: 569]. It is assumed that the results reported in these publications have been obtained with various known strains of MVA, since the viruses used essentially differ in their properties, particularly in their growth behavior in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic. MVA was further passaged by Bavarian Nordic and is designated MVA-BN, a representative sample of which was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein in their entirety.

MVA-BN can attach to and enter human cells where virally-encoded genes are expressed very efficiently. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), Antivir. Ther. 10(2):285-300; A. Cosma et al. (2003), Vaccine 22(1):21-9; M. Di Nicola et al. (2003), Hum. Gene Ther. 14(14):1347-1360; M. Di Nicola et al. (2004), Clin. Cancer Res., 10(16):5381-5390].

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [Boukamp et al (1988), J. Cell Biol. 106: 761-771], the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893, both of which are incorporated by reference herein in their entirety.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO 02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

MVA vectors useful for the invention can be prepared using methods known in the art, such as those described in WO/2002/042480 and WO/2002/24224, the relevant disclosures of which are incorporated herein by references.

In another aspect, replication deficient MVA viral strains may also be suitable such as strain MVA-572, MVA-575 or any similarly attenuated MVA strain. Also suitable can be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see WO 2011/092029).

In a preferred embodiment of the invention, the MVA vector(s) comprise a nucleic acid that encode one or more antigenic proteins selected from the group consisting of GPs of Zaire ebolavirus (EBOV), GPs of Sudan ebolavirus (SUDV), GPs of Marburg virus (MARV), the NP of Taï Forest virus and GPs or NPs substantially similar thereto.

The filovirus protein can be inserted into one or more intergenic regions (IGR) of the MVA. In certain embodiments, the IGR is selected from IGR07/08, IGR 44/45, IGR 64/65, IGR 88/89, IGR 136/137, and IGR 148/149. In certain embodiments, less than 5, 4, 3, or 2 IGRs of the recombinant MVA comprise heterologous nucleotide sequences encoding antigenic determinants of a filovirus envelope glycoprotein and/or a further filovirus protein. The heterologous nucleotide sequences may, additionally or alternatively, be inserted into one or more of the naturally occurring deletion sites, in particular into the main deletion sites I, II, III, IV, V, or VI of the MVA genome. In certain embodiments, less than 5, 4, 3, or 2 of the naturally occurring deletion sites of the recombinant MVA comprise heterologous nucleotide sequences encoding antigenic determinants of a filovirus envelope glycoprotein and/or a further filovirus protein.

The number of insertion sites of MVA comprising heterologous nucleotide sequences encoding antigenic determinants of a filovirus protein can be 1, 2, 3, 4, 5, 6, 7, or more. In certain embodiments, the heterologous nucleotide sequences are inserted into 4, 3, 2, or fewer insertion sites. Preferably, two insertion sites are used. In certain embodiments, three insertion sites are used. Preferably, the recombinant MVA comprises at least 2, 3, 4, 5, 6, or 7 genes inserted into 2 or 3 insertion sites.

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) [J. Sambrook et al., Cold Spring Harbor Laboratory Press (1989)], and techniques for the handling and manipulation of viruses are described in Virology Methods Manual [B. W. J. Mahy et al. (eds.), Academic Press (1996)]. Similarly, techniques and know-how for the handling, manipulation and genetic engineering of MVA are described in Molecular Virology: A Practical Approach [A. J. Davison & R. M. Elliott (Eds.), The Practical Approach Series, IRL Press at Oxford University Press, Oxford, UK (1993) (see, e.g., Chapter 9: Expression of genes by Vaccinia virus vectors)] and Current Protocols in Molecular Biology [John Wiley & Son, Inc. (1998) (see, e.g., Chapter 16, Section IV: Expression of proteins in mammalian cells using vaccinia viral vector)].

For the generation of the various recombinant MVAs disclosed herein, different methods can be applicable. The DNA sequence to be inserted into the virus can be placed into an E. coli plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within E. coli bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter.

Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repealed by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in E. coli or another bacterial species between a vaccinia virus genome, such as MVA, cloned as a bacterial artificial chromosome (BAC) and a linear foreign sequence flanked with DNA sequences homologous to sequences flanking the desired site of integration in the vaccinia virus genome.

The heterologous filovirus gene can be under the control of (i.e., operably linked to) one or more poxvirus promoters. In certain embodiments, the poxvirus promoter is a Pr7.5 promoter, a hybrid early/late promoter, or a PrS promoter, a PrS5E promoter, a synthetic or natural early or late promoter, or a cowpox virus ATI promoter.

Immunogenic Compositions

Immunogenic compositions are compositions comprising an immunologically effective amount of purified or partially purified adenovirus or MVA vectors for use in the invention. Said compositions can be formulated as a vaccine (also referred to as an "immunogenic composition") according to methods well known in the art. Such compositions may include adjuvants to enhance immune responses. The optimal ratios of each component in the formulation can be determined by techniques well known to those skilled in the art in view of the present disclosure.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The compositions of the invention may comprise any antigens. These antigenic peptides or polypeptides can include any sequences that are immunogenic such as, for example, tumor-specific antigens (TSAs), bacterial, viral, fungal, and protozoal antigens.

The compositions of the invention may comprise filovirus antigens or the priming or boosting inoculations may comprise other antigens. The other antigens used in combination with the adenovirus vectors of the invention are not critical to the invention and can be, for example, filovirus antigens and nucleic acids expressing them.

The immunogenic compositions useful in the invention can comprise adjuvants.

Adjuvants suitable for co-administration in accordance with the invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-IO, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intramuscular, subcutaneous, oral, intravenous, cutaneous, intramucosal (e.g., gut), intranasal or intraperitoneal routes.

Method for Enhancing an Immune Response

The invention provides an improved method of priming and boosting an immune response to any antigenic protein or immunogenic polypeptide thereof in a human subject using an MVA vector in combination with an adenoviral vector.

According to one general aspect of the invention, a method of enhancing an immune response in a human subject comprises:

a. administering to the human subject a first composition comprising an immunologically effective amount of a MVA vector comprising a first polynucleotide encoding an antigenic protein or an immunogenic polypeptide thereof for priming the immune response; and b. administering to the subject a second composition comprising an immunologically effective amount of an adenovirus vector comprising a second polynucleotide encoding the antigenic protein or an immunogenic polypeptide thereof for boosting the immune response;

to thereby obtain an enhanced immune response against the antigenic protein in the human subject.

According to embodiments of the invention, the enhanced immune response comprises an enhanced antibody response against the antigenic protein in the human subject.

Preferably, the enhanced immune response further comprises an enhanced CD4+ response or an enhanced CD8+ T cell response against the antigenic protein in the human subject. The enhanced CD4+ T cell response generated by a method according to an embodiment of the invention can be, for example, an increase or induction of a dominant CD4+ T cell response against the antigenic protein, and/or an increase or induction of polyfunctional CD4+ T cells specific to the antigenic protein in the human subject. The polyfunctional CD4+ T cells express more than one cytokine, such as two or more of IFN-gamma, IL-2 and TNF-alpha. The enhanced CD8+ T cell response generated by a method according to an embodiment of the invention can be, for example, an increase or induction of polyfunctional CD8+ T cells specific to the antigenic protein in the human subject.

More preferably, the enhanced immune response resulting from a method according to an embodiment of the invention comprises an enhanced CD4+ T cell response, an enhanced antibody response and an enhanced CD8+ T cell response, against the antigenic protein in the human subject.

In one or more embodiments of the invention, one or more MVA vectors are used to prime the immune response, and one or more rAd26 or rAd35 vectors are used to boost the immune response.

The antigens in the respective priming and boosting compositions (however many boosting compositions are employed) need not be identical, but should share antigenic determinants or be substantially similar to each other.

Administration of the immunogenic compositions comprising the vectors is typically intramuscular or subcutaneous. However other modes of administration such as intravenous, cutaneous, intradermal or nasal can be envisaged as well. Intramuscular administration of the immunogenic compositions can be achieved by using a needle to inject a suspension of the adenovirus vector. An alternative is the use of a needleless injection device to administer the composition (using, e.g., BIOJECTOR®) or a freeze-dried powder containing the vaccine.

For intravenous, cutaneous or subcutaneous injection, or injection at the site of affliction, the vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

Typically, administration will have a prophylactic aim to generate an immune response against an antigen before infection or development of symptoms. Diseases and disorders that can be treated or prevented in accordance with the invention include those in which an immune response can play a protective or therapeutic role. In other embodiments, the MVA and adenovirus vectors can be administered for post-exposure prophylactics.

The immunogenic compositions containing the MVA vectors are administered to a subject, giving rise to an immune response in the subject. An amount of a composition sufficient to in induce a detectable immune response is defined to be an "immunologically effective dose." As shown below, the immunogenic compositions of the invention induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of MVA and adenovirus vectors and optional formulation of such particles into compositions, the vectors can be administered to an individual, particularly a human.

In one exemplary regimen, the adenovirus vector is administered (e.g., intramuscularly) in a volume ranging between about 100 µl to about 10 ml containing concentrations of about $10^4$ to $10^{12}$ virus particles/ml. Preferably, the adenovirus vector is administered in a volume ranging between 0.25 and 1.0 ml. More preferably the adenovirus vector is administered in a volume of 0.5 ml.

Typically, the adenovirus is administered in an amount of about $10^9$ to about $10^{12}$ viral particles (vp) to a human subject during one administration, more typically in an amount of about $10^{10}$ to about $10^{12}$ vp. In a preferred embodiment, the adenovirus vector is administered in an amount of about $5\times10^{10}$ vp. In another preferred embodiment, the adenovirus vector is administered in an amount of about $0.8\times10^{10}$ vp. In another preferred embodiment, the adenovirus vector is administered in an amount of about $2\times10^{10}$ vp. In another preferred embodiment, the adenovirus vector is administered in an amount of about $4\times10^{10}$ vp. In certain embodiments, adenoviruses are formulated as a trivalent composition, wherein three adenoviruses with each a different insert, are mixed together. In a trivalent composition, each distinct adenovirus is preferably present in an amount of about $4\times10^{10}$ vp. In said trivalent composition, the total number of adenovirus particles per dose amounts to about $1.2\times10^{11}$ vp. In another preferred embodiment, each distinct adenovirus in the trivalent composition is present in an amount of about $1\times10^{11}$ vp. In said trivalent composition the total number of adenovirus particles per dose then amounts to about $3\times10^{11}$ vp. The initial vaccination is followed by a boost as described above.

In one exemplary regimen, the MVA vector is administered (e.g., intramuscularly) in a volume ranging between about 100 µl to about 10 ml of saline solution containing a dose of about $1\times10^7$ TCID$_{50}$ to $1\times10^9$ TCID$_{50}$ (50% Tissue Culture Infective Dose) or Inf.U. (Infectious Unit). Preferably, the MVA vector is administered in a volume ranging between 0.25 and 1.0 ml. More preferably the MVA vector is administered in a volume of 0.5 ml.

Typically, the MVA vector is administered in a dose of about $1\times10^7$ TCID$_{50}$ to $1\times10^9$ TCID$_{50}$ (or Inf.U.) to a human subject during one administration. In a preferred embodiment, the MVA vector is administered in an amount of about $5\times10^7$ TCID$_{50}$ to $5\times10^8$ TCID$_{50}$ (or Inf.U.). In a more preferred embodiment, the MVA vector is administered in an amount of about $5\times10^7$ TCID$_{50}$ (or Inf.U.). In a more preferred embodiment, the MVA vector is administered in an amount of about $1\times10^8$ TCID$_{50}$ (or Inf.U.). In another preferred embodiment, the MVA vector is administered in an amount of about $1.9\times10^8$ TCID$_{50}$ (or Inf.U). In yet another preferred embodiment, the MVA vector is administered in an amount of about $4.4\times10^8$ TCID$_{50}$ (or Inf.U.). In a more preferred embodiment, the MVA vector is administered in an amount of about $5\times10^8$ TCID$_{50}$ (or Inf.U.)

The composition can, if desired, be presented in a kit, pack or dispenser, which can contain one or more unit dosage forms containing the active ingredient. The kit, for example, may comprise metal or plastic foil, such as a blister pack. The kit, pack, or dispenser can be accompanied by instructions for administration.

The compositions of the invention can be administered alone or in combination with other treatments, either simultaneously or sequentially dependent upon the condition to be treated.

Boosting compositions are generally administered once or multiple times, weeks or months after administration of the priming composition, for example, about 1 or 2 weeks or 3 weeks, or 4 weeks, or 6 weeks, or 8 weeks, or 12 weeks, or 16 weeks, or 20 weeks, or 24 weeks, or 28 weeks, or 32 weeks or one to two years.

Preferably, the initial boosting inoculation is administered 1-12 weeks or 2-12 weeks after priming, more preferably 1, 2, 4 or 8 weeks after priming. In a preferred embodiment, the initial boosting inoculation is administered 4 or 8 weeks after priming. In additional preferred embodiments, the initial boosting is conducted at least 1 week, or at least 2 weeks, or at least 4 weeks after priming. In still another preferred embodiment, the initial boosting is conducted 4-12 weeks or 4-8 weeks after priming.

In a more preferred embodiment according to this method, an MVA vector is used for the priming followed by a boosting with an rAd26 vector. Preferably, the boosting composition is administered 1-12 weeks after priming, more preferably 1, 2, 4 or 8 weeks after priming. In a preferred embodiment, the boosting composition is administered 8 weeks after priming. In another preferred embodiment, the boosting composition is administered 1 week after priming. In another preferred embodiment, the boosting composition is administered 2 weeks after priming. In another preferred embodiment, the boosting composition is administered 4 weeks after priming.

One or more additional boosting administrations can be performed after the initial boosting.

In a preferred embodiment, the boosting composition comprises an Ad26 vector.

In one embodiment, the invention relates to a method of enhancing an immune response against a tumor in a human subject. The method comprises:
 a. administering to the human subject a first composition comprising an immunologically effective amount of a MVA vector comprising a first polynucleotide encoding an antigenic protein produced by a cell of the tumor, a substantially similar antigenic protein, or an immunogenic polypeptide thereof for priming the immune response; and
 b. administering to the subject a second composition comprising an immunologically effective amount of an adenovirus vector comprising a second polynucleotide encoding the antigenic protein, the substantially similar antigenic protein, or an immunogenic polypeptide thereof for boosting the immune response;
 to thereby obtain an enhanced immune response against the tumor in the human subject.

Preferably, the enhanced immune response provides the human subject with a protective immunity against the tumor.

In a preferred embodiment the boosting step is conducted 1-12 weeks or 2-12 weeks after the first priming step. The boosting step can also be conducted later than 12 weeks after the priming step. In additional preferred embodiments, the boosting step is conducted at least 2 weeks or at least 4 weeks after the priming step. In still other preferred embodiments, the boosting step is conducted 4-12 weeks or 4-8 weeks after the priming step.

In another embodiment, the boosting step is repeated one or more times after the initial boosting administration.

In another preferred embodiment, the adenovirus vector is an Ad26 vector.

The antigenic protein produced by a cell of the tumor can be any tumor antigen. In a preferred embodiment, the tumor antigen is a tumor-specific antigen that is present only on tumor cells. The tumor antigen can also be a tumor-associated antigen that is present on some tumor cells and also some normal cells.

According to another embodiment, the invention relates to a method of enhancing an immune response against at least one subtype of filovirus in a human subject. The method comprises:
 a. administering to the human subject a first composition comprising an immunologically effective amount of a MVA vector comprising a polynucleotide encoding an antigenic protein of the at least one filovirus subtype, a substantially similar antigenic protein, or an immunogenic polypeptide thereof, for priming the immune response; and
 b. administering to the subject a second composition comprising an immunologically effective amount of an adenovirus vector comprising a polynucleotide encoding an antigenic protein of the at least one filovirus subtype, a substantially similar antigenic protein, or an immunogenic polypeptide thereof, for boosting the immune response;
 to thereby obtain an enhanced immune response against the at least one subtype of filovirus in the human subject.

Preferably, the enhanced immune response provides the human subject a protective immunity against the at least one subtype of filovirus.

In a preferred embodiment the boosting step is conducted 1-12 weeks or 2-12 weeks after the first step, more preferably 1, 2, 4, or 8 weeks after priming. In additional preferred embodiments, the boosting step is conducted at least 1 week or at least 2 weeks after the priming. In still other preferred embodiments, the boosting step is conducted 4-12 weeks or 4-8 weeks after the priming.

The boosting step can also be conducted later than 12 weeks after priming.

In another embodiment, the boosting step is repeated one or more times after the initial boosting administration, such as 6 months, 1 year, 1.5 years, 2 years, 2.5 years, or 3 years after priming.

In another preferred embodiment, the adenovirus vector is an Ad26 vector.

In yet another preferred embodiment, the antigenic protein is a glycoprotein or a nucleoprotein of a filovirus subtype.

In one embodiment of the invention, the MVA vector in the first composition comprises a polynucleotide encoding antigenic proteins derived from more than one filovirus subtypes. More preferably, the MVA vector in the first composition comprises a polynucleotide encoding four antigenic proteins from four filovirus subtypes having the amino acid sequences of SEQ ID NOs: 1, 2, 4 and 5, or immunogenic polypeptides thereof.

In another embodiment of the invention, the second composition comprises at least one adenovirus vector comprising a polynucleotide encoding an antigenic protein derived from a filovirus subtype that is same or different from the filovirus subtype encoded by the MVA vector. For example, the adenovirus vector can comprise a polynucleotide encoding an antigenic protein having the amino acid sequence selected from the group consisting of SEQ ID NOs: 1-5. Preferably, the second composition can comprise more than one adenovirus vectors encoding more than one antigenic proteins or immunogenic polypeptides thereof from more than one filovirus subtypes. For example, the second composition can comprise one to three adenovirus vectors encoding one to three of the antigenic proteins have the amino acid sequences of SEQ ID NOs: 1, 2 and 3.

EXAMPLES

The following examples are offered to illustrate, but not to limit the claimed invention.

Example 1

An animal study was conducted with a goal of identifying a multivalent filovirus vaccine with real efficacy 80% against multiple [e.g., Marburg, Ebola (aka Zaire) & Sudan] Filoviruses for continued advance development. The study tested an extended vaccination schedule using two or three vaccinations and impact of using heterologous (as opposed to homologous) vaccine combinations on subsequent NHP immune responses to the target Filoviruses. The vaccinated NHP was challenged with Ebola virus Kikwit to test the efficacy of the applied vaccinations.

Animal Manipulations

These studies complied with all applicable sections of the Final Rules of the Animal Welfare Act regulations (9 CFR Parts 1, 2, and 3) and *Guide for the Care and Use of Laboratory Animals*—National Academy Press, Washington D.C. Eight Edition (the Guide).

A total of 16 Cynomolgus macaques (Macaca fascicularis) (NHPs) (12 males and 4 females), Mauritian-origin, cynomolgus macaques, 4-5 years old, approx. 4-8 kg each, were purchased from PrimGen (Hines, Ill.). Animals were experimentally naive to Reston virus (RESTV) by ELISA prior to vaccination. Animals with prior exposure to *Mycobacterium tuberculosis*, Simian Immunodeficiency Virus (SIV), Simian T-Lymphotropic Virus-1 (STLV-1), Macacine herpesvirus 1 (Herpes B virus), and Simian Retrovirus (SRV1 and SRV2) were excluded, and active infections with *Salmonella* and *Shigella* were tested, and confirmed negative for *Mycobacterium tuberculosis*.

Filoviruses are Risk Group 4 (High Containment) Pathogens; therefore all manipulations involving Zaire ebolavirus, Sudan ebolavirus, or Marburgviruses were carried out in the CDC-accredited Biosafety Level (BSL)-4/Animal Biosafety Level (ABSL-4) containment facility.

Vaccine Materials

The rAd vectors were manufactured by Crucell Holland B.V. They are purified E1/E3-deleted replication deficient recombinant Adenovirus type 26 or type 35 vaccine vectors (Ad26 and Ad35, respectively) containing the Filovirus Glycoprotein (GP) genes inserted at the E1 position. These vectors were rescued in PER.C6® cells, plaque purified, upscaled and then purified by a two-step CsCl banding procedure and subsequently formulated in a TRIS-based formulation buffer and stored below −65° C. Release for in vivo use of these vectors includes bioburden test, low endotoxin level (<5 EU/ml) and confirmation of expression and integrity of the transgene.

In particular, the rAd vectors expressed EBOV Mayinga GP (SEQ ID NO:1), SUDV Gulu GP (SEQ ID NO:2) and MARV Angola GP (SEQ ID NO:3). Each rAd vector expressed one single antigenic protein (GP).

The MVA vectors were manufactured by Bavarian Nordic. In particular, the MVA-multi vector (MVA-BN-Filo) expressed 4 different antigenic proteins: EBOV Mayinga GP (SEQ ID NO:1); SUDV Gulu GP (SEQ ID NO:2); MARV Musoke GP (SEQ ID NO:4); and Taï forest virus (TAFV) NP (SEQ ID NO:5).

The vaccine materials were stored at −80° C. in a controlled temperature freezer.

Vaccination and Experimental Design

See FIGS. 1 and 2 for the study grouping and experimental design.

Cynomolgus macaques (Macaca fascicularis) (NHPs) were vaccinated using two different vaccine platforms, 2 animals per group, in addition to a control group consisting of two naïve (empty vector) challenge controls. Animals were first vaccinated with the recombinant vector(s) in groups shown in FIG. 1. Each macaque was anesthetized and received an intramuscular (IM) injection of the vaccine into the left hind thigh. Priming and boosting doses were given 4 or 8 weeks apart (FIG. 1). Each dose of adenoviruses consisted of a single IM injection into the left posterior thigh. The MVA vectors were administered subcutaneously.

EDTA or heparin whole blood were shipped overnight at room temperature to Texas Biomed on D28, D56 and D63. Additionally, Heparin or EDTA whole blood was collected on D77 while animals were housed at Texas Biomed. At all these time-points, EDTA whole blood will be processed for PBMC and plasma at Texas Biomed.

PBMC were used in an IFN-g ELISPOT assay using Ebola Zaire peptide pools 1 and 2, Sudan Gulu peptide pools 1 and 2, an Ebolavirus consensus peptide pool, Marburg Angola peptide pool 1 and 2 and a Marburgvirus consensus peptide pool, together with a DMSO only negative control and an anti-CD3 stimulation positive control. All stimulations were performed in duplicate, for a total of 20 wells per NHP.

Additionally, whole blood without anticoagulant was processed for serum at Bioqual on D0, D28, D56 and D68, and on D77 at Texas Biomed. Aliquots of the serum collected at Bioqual will be sent frozen to Texas Biomed on D68. Each serum was assayed in a ZEBOV GP specific ELISA. Additionally, serum from D0, D56 and D77 were assayed in a SEBOV GP and a MARVA GP specific ELISA (two different assays).

TABLE 1

Parameters measured before challenge with Ebola virus

| Parameter | Study weeks | | | | | |
|---|---|---|---|---|---|---|
| | 0 | 4 | 8 | 9 | 10 | 11 |
| PBMC and plasma processing | | X | X | X | | X |
| ZEBOV GP ELISA - all animals | X | X | X | | X | X |
| SEBOV GP ELISA - all animals | X | | X | | | X |
| MARVA GP ELISA - all animals | X | | X | | | X |
| Filovirus ELISPOT - all animals | | X | X | X | | X |

Filovirus Inoculum for Animal Challenges

As shown in FIG. 2, about 4 weeks after the boosting vaccination, the animals were challenged with EBOV. In particular, EBOV kikwit-9510621 was used for animal challenges and was supplied by Texas Biomed. A second cell-culture passage (P2) of EBOV kikwit-9510621 was obtained from Dr. Tom Ksiazek (at NIAID's WRCEVA at UTMB's Health Galveston National Laboratory) in 2012 and propagated at Texas Biomed for a third time in Vero E6 cells and had a titer of $2.1 \times 10^5$ PFU/ml. EBOV kikwit-9510621. LOT No. 2012099171.

Titer at harvest: $2.1 \times 10^5$ PFU/ml was used for the study.

The challenge stock has been confirmed to be wild-type EBOV kikwit 9510621 by deep sequencing with only 1 SNP difference from the Genbank P2 consensus sequence. The challenge stock was stored in liquid nitrogen vapor phase as 500±50 µl aliquots containing media (MEM) containing 10% FBS. For a 100 PFU challenge, the filovirus challenge agent was diluted to a target dose of 200 PFU/ml in phosphate buffered saline. Briefly, stock virus was diluted via three consecutive 1:10 dilutions in PBS to achieve a 200 PFU/ml challenge material concentration. A total of 0.5 ml of challenge material was given to each animal.

Prior to virus injection, monkeys were sedated via intramuscular injection with Telazol (2 to 6 mg/kg; 5 to 8 mg/kg ketamine IM prn for supplemental anesthesia). On Study Day 0, blood was collected and each monkey was subsequently challenged with a targeted dose of 100 PFU of EBOV in a 0.5 ml volume via intramuscular injection in the right deltoid muscle of the arm. The challenge site was recorded.

Following virus administration, each monkey was returned to its home cage and observed until it has recovered from anesthesia (sternal recumbancy/ability to maintain an upright posture). Endpoints in this study were survival/nonsurvival. Nonsurvival is defined by an animal having terminal illness or being moribund. Animals' health was evaluated on a daily clinical observation score sheet.

Anti-EBOV GP IgG ELISA

Figure 6:
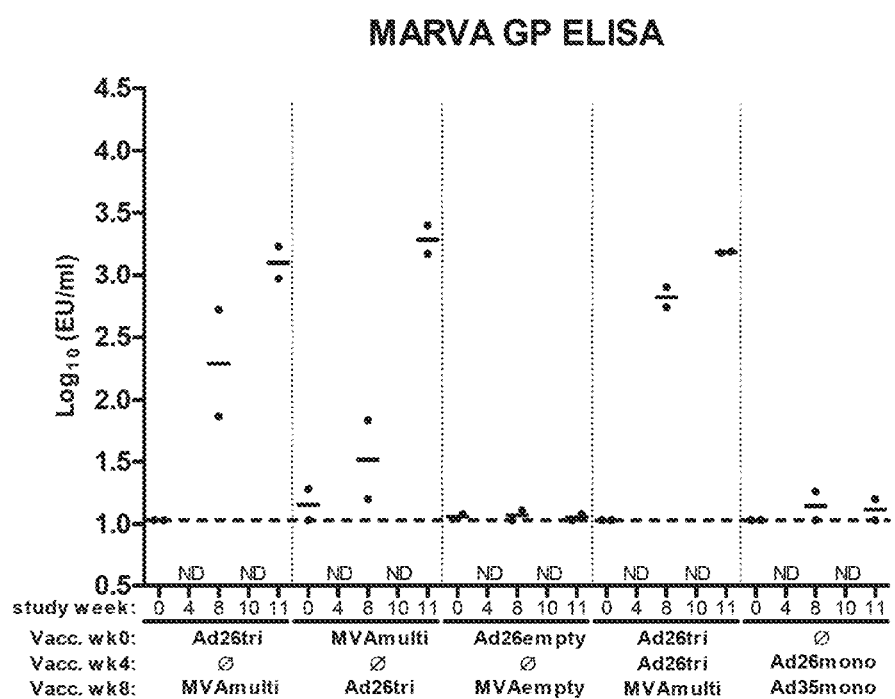

Filovirus-specific humoral response was determined at time points described in table 1 by a modified enzyme-linked immunosorbent assay (ELISA), as previously described in Sulivan et al. (2006) (Immune protection of nonhuman primates against Ebola virus with single low-dose adenovirus vectors encoding modified GPs. PLoS Medicine 3, e177), which is incorporated by reference herein in its entirety. Briefly, ELISA plates were coated over night with Galanthus Nivalis Lectin at 10 µg/ml. Then, after blocking, the plates were coated with either an Ebola or a Marburg strain specific GP supernatant. These supernatants were produced by transient transfection of Hek293T with expression plasmids coding for filovirus glycoprotein deleted of the transmembrane domain and cytoplasmic tail. Monkey serum samples were tested in a 4-fold dilution series starting at 1:50. Bound IgG was detected by colorimetry at 492 nm. Relative serum titers were calculated against a filovirus glycoprotein strain specific reference serum. The results of the Elisa assay are shown in FIGS. 4-6.

IFN-g ELISPOT Assay

Filovirus-specific cellular immune response was determined at time points described in table 1 by interferon gamma Enzyme-linked immunospot assay (ELISPOT) as previously described in Ophorst et al. 2007 (Increased immunogenicity of recombinant Ad35-based malaria vaccine through formulation with aluminium phosphate adjuvant. Vaccine 25, 6501-6510), which is incorporated by reference herein in its entirety. The peptide pools used for stimulation for each Ebola and Marburg strain glycoprotein consist of 15-mers overlapping by 11 amino acids. To minimize undesired effects of a too high number of peptides in a pool, each glycoprotein peptide pool was divided into two, one N-terminal and one C-terminal half.

Figure 7:
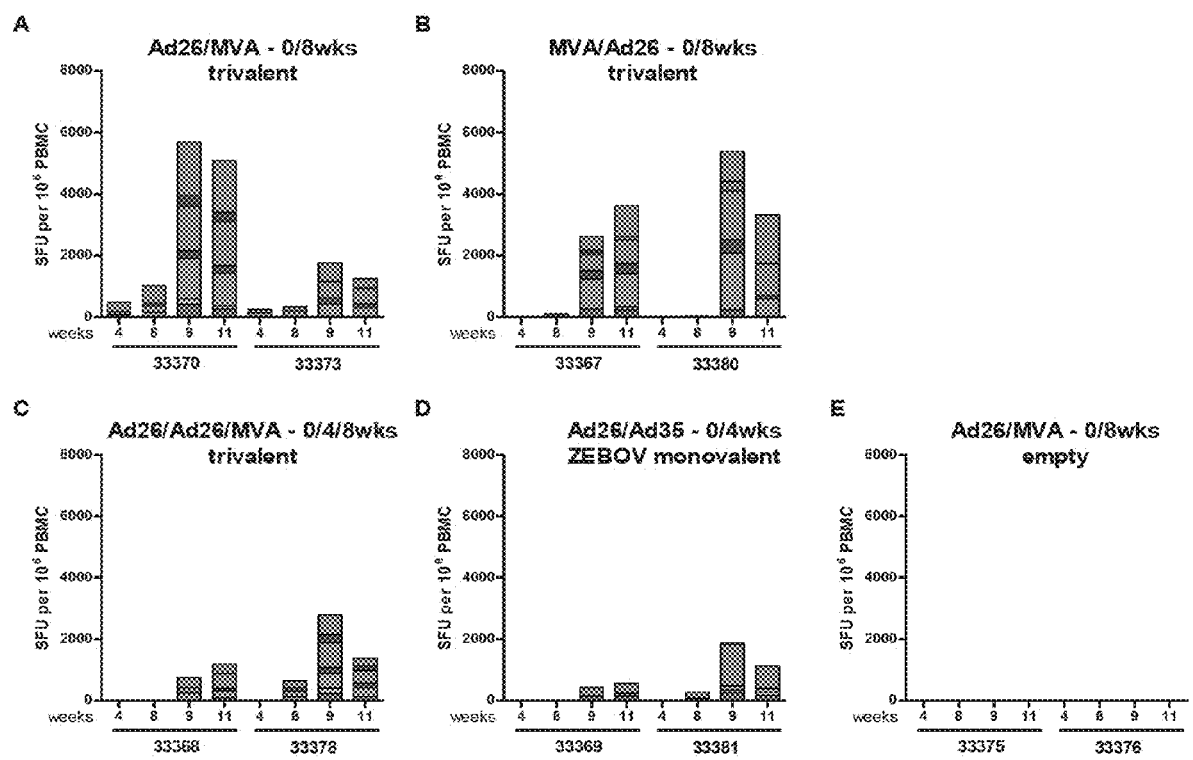

Peptides that overlap with more than nine consecutive amino acids within three Ebolavirus (Zaire, Sudan and Tat Forest) or two Marburgvirus (Marburg and Ravn viruses) were combined in a consensus pool. The peptide pools and single peptides were used at a final concentration of 1 µg/ml for each single peptide. The results of the ELISPOT assay are shown in FIG. 7.

As shown by results summarized in FIGS. 3-7, the animal study herein demonstrated the utility of rAd and MVA vectors in prime-boost combinations for preventing filovirus infections in primates. In particular, the administration of one or more rAd26 vectors expressing GP(s) of one or more types of filoviruses or MVA vectors expressing multiple filovirus antigens resulted in efficient priming of the humoral response to the one or more types of filoviruses. After boost immunization at week 8 with the heterologous vector, all vaccine regimes induced a similar humoral and cellular immune response to the one or more types of filoviruses and provided 100% protection against a highly pathogenic Ebola Zaire challenge.

Example 2

A second NHP study was performed to confirm the immunogenicity and protective efficacy of 2 prime-boost regimens at 0-4 week and at 0-8 week intervals. One comprising a monovalent Ad26.ZEBOV vaccine as a prime and a MVA-BN-Filo as a boost; the other one comprising a MVA-BN-Filo as a prime and an Ad26.ZEBOV as a boost. All immunizations were Intra muscular. Ad26.ZEBOV ($5 \times 10^{10}$ vp) was used as a prime for the 0-8 week regimen, and was combined with a boost of $1 \times 10^8$ $TCID_{50}$ of MVA-BN-Filo (4 NHPs) and $5 \times 10^8$ $TCID_{50}$ MVA-BN-Filo (4 NHPs) to assess the impact of a standard and a high dose of MVA in this regimen. Two additional groups of 4 NHPs were primed with $1 \times 10^8$ $TCID_{50}$ of MVA-BN-Filo and $5 \times 10^8$ $TCID_{50}$ MVA-BN-Filo, respectively; in both cases followed by a boost with Ad26.ZEBOV ($5 \times 10^{10}$ vp) after 4 weeks, to test the impact of the MVA-BN-Filo dose as a prime in a 4-week regimen. In addition, 2 NHPs were primed with Ad26.ZEBOV ($5 \times 10^{10}$ vp) followed by $1 \times 10^8$ $TCID_{50}$ of MVA-BN-Filo. Finally, 2 NHPs were immunized with empty Ad26 vector (not expressing any Filovirus antigens, $5 \times 10^{10}$ vp IM) and TBS as negative immunization control for the study. All animals were challenged 4 weeks after the last immunization with 100 pfu of EBOV Kikwit 1995 wild-type P3 challenge virus. The grouping of this study is summarized in Table 2.

TABLE 2

Experimental Grouping of Protection Study in Non-human Primates Challenged With EBOV

| Group | Immunization 1 (Dose 1) | Immunization 2 (Dose 2) | Immunization Schedule (Weeks) | Challenge After 4 Weeks | Survival Ratio (%) |
|---|---|---|---|---|---|
| 1/A | Ad26.empty ($5 \times 10^{10}$ vp) | MVA negative control (TBS) | 0-8 | EBOV (Kikwit) | 0/2 (0%) |
| 2/B | Ad26.ZEBOV ($5 \times 10^{10}$ vp) | MVA-BN-Filo ($5 \times 10^8$ $TCID_{50}$) | 0-8 | EBOV (Kikwit) | 4/4 (100%) |
| 3/C | MVA-BN-Filo ($5 \times 10^8$ $TCID_{50}$) | Ad26.ZEBOV ($5 \times 10^{10}$ vp) | 4-8 | EBOV (Kikwit) | 2/4 (50%) |
| 4/D | Ad26.ZEBOV ($5 \times 10^{10}$ vp) | MVA-BN-Filo ($1 \times 10^8$ $TCID_{50}$) | 0-8 | EBOV (Kikwit) | 4/4 (100%) |
| 5/E | MVA-BN-Filo ($1 \times 10^8$ $TCID_{50}$) | Ad26.ZEBOV ($5 \times 10^{10}$ vp) | 4-8 | EBOV (Kikwit) | 2/4 (50%) |
| 6/F | Ad26.ZEBOV ($5 \times 10^{10}$ vp) | MVA-BN-Filo ($1 \times 10^8$ $TCID_{50}$) | 4-8 | EBOV (Kikwit) | 2/2 (100%) |

Abbreviations:
TBS: Tris-buffered saline;
$TCID_{50}$: 50% tissue culture infective dose;
vp: viral particles.
100% survival are in bold.

Immunogenicity

Figure 20:
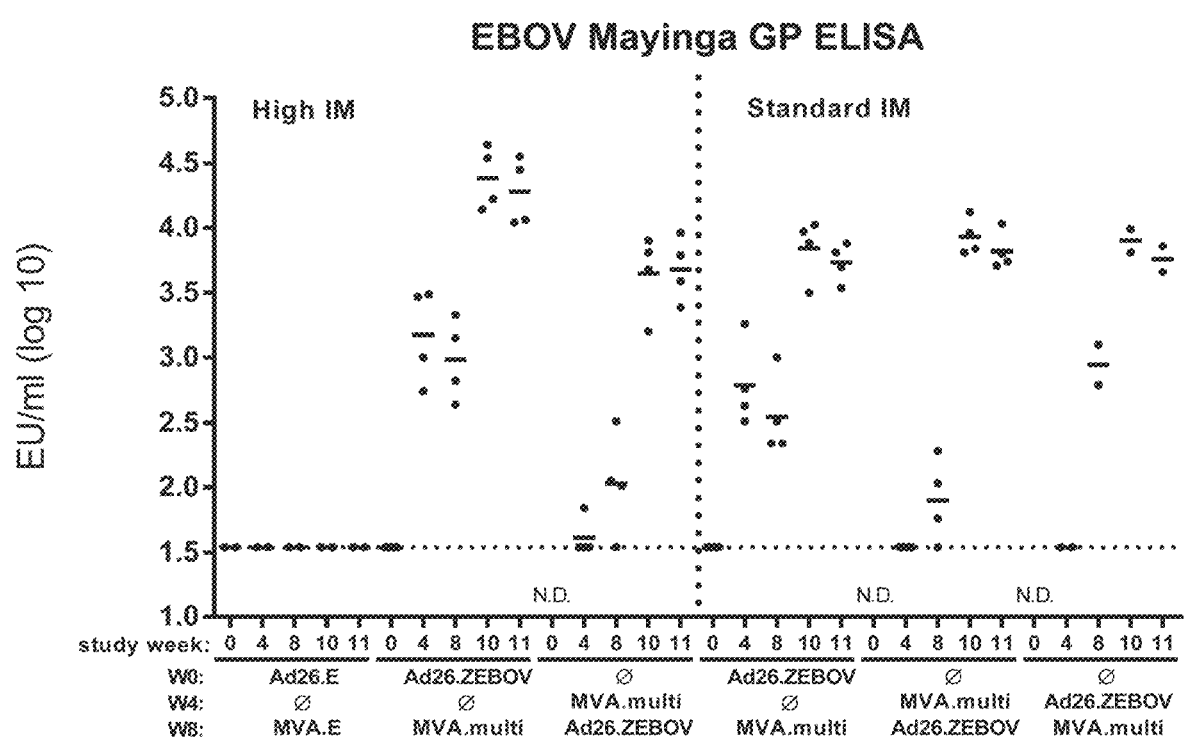

The immune response in NHP is characterized with respect to Filovirus GP-binding and neutralizing antibodies (ELISA) as well as cytokine producing T cells (ELISpot).
ELISA:

EBOV Mayinga GP reactive antibodies were analyzed by GP-specific ELISA for all timepoints (see FIG. 20). The Anti-EBOV GP IgG ELISA was performed as described in experiment 1. ELISA titers were not observed in control-vaccinated animals. The vaccine regimens were immunogenic in all animals. The highest titers were observed in Group B, receiving Ad26.ZEBOV and a high dose of MVA-BN-Filo with an 8-week interval.

Protective Efficacy

Both 8-week Ad26.ZEBOV/MVA-BN-Filo prime/boost regimens resulted in complete survival after EBOV challenge, irrespective of the dose of MVA-BN-Filo ($1\times10^8$ $TCID_{50}$ or $5\times10^8$ $TCID_{50}$). Additionally, a 4-week regimen of Ad26.ZEBOV/MVA-BN-Filo gave protection in 2 out of 2 NHPs. Both 4-week MVA-BN-Filo/Ad26.ZEBOV regimens gave protection in 2 out of 4 NHPs.

Example 3

A clinical study is performed in humans for evaluating the safety, tolerability and immunogenicity of regimens using MVA-BN-Filo at a dose of $1\times10^8$ $TCID_{50}$ and Ad26.ZEBOV at a dose of $5\times10^{10}$ vp. The study consisted of two parts.

ability and immunogenicity of a regimen with Ad26.ZEBOV at a dose of $5\times10^{10}$ vp as prime, and MVA-BN-Filo at a dose of $1\times10^8$ $TCID_{50}$ as boost 14 days later, and is conducted in 15 healthy adult subjects.

The study consists of a vaccination period in which subjects are vaccinated at baseline (Day 1) followed by a boost on Day 15, 29 or 57, and a post-boost follow-up until all subjects have had their 21-day post-boost visit (Day 36, 50 or 78) or discontinued earlier.

Subjects in the main study are enrolled into 4 different groups of 18 healthy subjects each. Overall, subjects are randomized within a group in a 5:1 ratio to receive active vaccine or placebo (0.9% saline) through IM injections (0.5 ml) as follows:

MVA-BN-Filo ($1\times10^8$ $TCID_{50}$) on Day 1, followed by a booster of Ad26.ZEBOV ($5\times10^{10}$ vp) on Day 29 (Group 1) or Day 57 (Group 2), or Ad26.ZEBOV ($5\times10^{10}$ vp) on Day 1, followed by a booster of MVA-BN-Filo ($1\times10^8$ $TCID_{50}$) on Day 29 (Group 3) or Day 57 (Group 4).

The 15 subjects in the substudy receive active vaccine through IM injections (0.5 ml) as follows:

Ad26.ZEBOV ($5\times10^{10}$ vp) on Day 1, followed by a booster of MVA-BN-Filo ($1\times10^8$ $TCID_{50}$) on Day 15 (Group 5).

The exemplary study vaccination schedules are summarized in Table 3.

TABLE 3

Study Vaccination Schedules

| Group | N | | Day 1 | Day 15 | Day 29 | Day 57 |
|---|---|---|---|---|---|---|
| 1 | 18 | 15 | MVA-BN-Filo $1 \times 10^8$ $TCID_{50}$ | — | Ad26.ZEBOV $5 \times 10^{10}$ vp | — |
|   |    | 3  | placebo (0.9% saline) | — | placebo (0.9% saline) | — |
| 2 | 18 | 15 | MVA-BN-Filo $1 \times 10^8$ $TCID_{50}$ | — | — | Ad26.ZEBOV $5 \times 10^{10}$ vp |
|   |    | 3  | placebo (0.9% saline) | — | — | placebo (0.9% saline) |
| 3 | 18 | 15 | Ad26.ZEBOV $5 \times 10^{10}$ vp | — | MVA-BN-Filo $1 \times 10^8$ $TCID_{50}$ | — |
|   |    | 3  | placebo (0.9% saline) | — | placebo (0.9% saline) | — |
| 4 | 18 | 15 | Ad26.ZEBOV $5 \times 10^{10}$ vp | — | — | MVA-BN-Filo $1 \times 10^8$ $TCID_{50}$ |
|   |    | 3  | placebo (0.9% saline) | — | — | placebo (0.9% saline) |
| 5 |    | 15 | Ad26.ZEBOV $5 \times 10^{10}$ vp | MVA-BN-Filo $1 \times 10^8$ $TCID_{50}$ | — | — |

N: number of subjects to receive study vaccine;
$TCID_{50}$: 50% Tissue Culture Infective Dose;
vp: viral particles The main study is a randomized, placebo-controlled, observer-blind study being conducted in 72 healthy adult subjects who never received an experimental Ebola candidate vaccine before and have no known exposure to an Ebola virus or diagnosis of Ebola disease. In this study 4 regimens are tested: 2 regimens have MVA-BN-Filo as prime and Ad26.ZEBOV as boost at a 28- or 56-day interval, and 2 regimens have Ad26.ZEBOV as prime and MVA-BN-Filo as boost at a 28- or 56-day interval.

The sub-study consists of an open-label, uncontrolled non-randomized treatment arm evaluating the safety, toler- Safety is assessed by collection of solicited local and systemic adverse events, unsolicited adverse events and serious adverse events, and by physical examination. In addition, standard chemistry, hematologic (including coagulation parameters) and urinalysis parameters are assessed at multiple time points.

Immunogenicity is assessed using the immunologic assays summarized in Tables 4 and 5. The exploratory assay package may include, but is not limited to, the listed assays.

TABLE 4

Summary of Immunologic Assays (Serology)

| Assay | Purpose |
| --- | --- |
| Secondary endpoints | |
| Virus neutralization assay | Analysis of neutralizing antibodies to EBOV GP |
| ELISA | Analysis of antibodies binding to EBOV GP |
| Exploratory endpoints | |
| Adenovirus/MVA neutralization assay | Neutralizing antibodies to adenovirus/MVA |
| Molecular antibody characterization | Analysis of anti-EBOV GP, SUDV GP, MARV GP and/or TAFV NP antibody characteristics, including IgG subtyping |
| Exploratory ELISA | Analysis of binding antibodies to a different source of EBOV GP |

EBOV: Ebola virus;
ELISA: enzyme-linked immunosorbent assay;
GP: glycoprotein;
IgG: Immunoglobulin G;
MARV: Marburg virus;
MVA: Modified Vaccinia Ankara;
NP: nucleoprotein;
SUDV: Sudan virus;
TAFV: Taï Forest virus

TABLE 5

Summary of Immunologic Assays (Cellular)

| Assay | Purpose |
| --- | --- |
| Secondary endpoints | |
| ELISpot | T-cell IFN-γ responses to EBOV GP |
| Exploratory endpoints | |
| ICS of frozen PBMC | Analysis of T-cell responses to EBOV GP, SUDV GP, MARV GP and/or TAFV NP (including CD4/8, IL-2, IFN-γ, TNF-α and/or activation markers) |
| ICS and/or ELISpot of fresh PBMC | Analysis of T cell responses to EBOV GP including CD4-positive and low-magnitude T cell responses |

EBOV: Ebola virus; ELISpot: enzyme-linked immunospot; GP: glycoprotein; ICS: intracellular cytokine staining; IFN: interferon; IL: interleukin; MARV: Marburg virus; NP: nucleoprotein; PBMC: peripheral blood mononuclear cells; SUDV: Sudan virus; TAFV: Taï Forest virus; TNF: tumor necrosis factor Safety Assessment Safety was assessed by collection of solicited local and systemic adverse events, unsolicited adverse events and serious adverse events, and by physical examination. In addition, standard chemistry, hematologic (including coagulation parameters) and urinalysis parameters were assessed at multiple time points.

The safety data from this first in human showed that both vaccines appear to be well-tolerated at this stage with transient reactions normally expected from vaccination. No significant adverse events were associated with the vaccine regimen. The majority of events were mild, occurring one to two days post-vaccination, and lasting one to two days on average. Very few cases of fever were observed.

Assessment of Immune Response

Immunogenicity was assessed up to 21 days post-boost immunization using an ELISA assay to analyze antibodies binding to EBOV GP, an ELISpot assay to analyze an EBOV GP-specific T cell response, and ICS assays to detect CD4+ and CD8+ T-cell responses to EBOV GP. Samples for the analysis of the humoral and cellular immune response induced by the study vaccines were collected on Days 1, 8, 29, 36 and 50 in Groups 1 and 3 and on Days 1, 8, 29, 57, 64 and 78 for Groups 2 and 4.

Assessment of Humoral Immune Response

Figure 8:
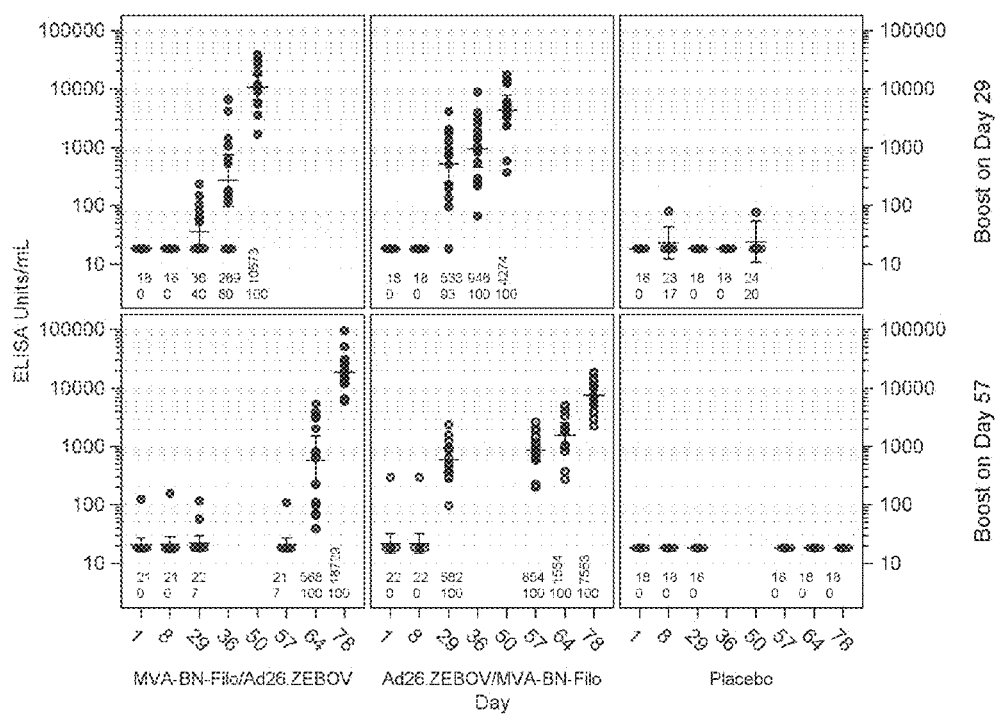

The binding antibody responses induced by study vaccines was assessed by an anti-EBOV GP ELISA assay (FIG. 8). Importantly, all subjects who have received a vaccine regimen showed seroconversion at 21 days post-boost immunization. While the EBOV GP-specific immune response post-prime with MVA-BN-Filo was only observed at low levels in 7 to 40% of the subjects, a strong antigen-specific response was observed post-boost with Ad26.ZEBOV administered at 28 days or 56 days post-prime. Surprisingly, this response is of higher magnitude than the one induced by the reverse vaccine regimen at the same prime-boost time interval (Group 3 and Group 4, Ad26.ZEBOV prime followed by MVA-BN-Filo boost 28 or 56 days later, respectively) at 21 days post-boost immunization [Geometric mean titers with 95% confidence interval of EU/mL 10573 (6452; 17327) and 4274 (2350; 7775) for groups 1 and 3, respectively, and 18729 (12200; 28751) and 7553 (511; 1115) for groups 2 and 4, respectively].

It must be noted that in nonhuman primate (NHP), boosting an MVA prime with Ad26 had resulted in an EBOV GP-specific immune response, that was comparable in magnitude to that induced by the reverse vaccine regimen (Ad/MVA), at the same prime-boost time interval (see FIG. 4) or that was inferior in magnitude (FIG. 20). Thus, the immune responses observed for one specific prime-boost regimen in NHP were not predictive for the immune responses observed following that same prime-boost regimen in humans.

Assessment of Cellular Immune Response

Figure 9:
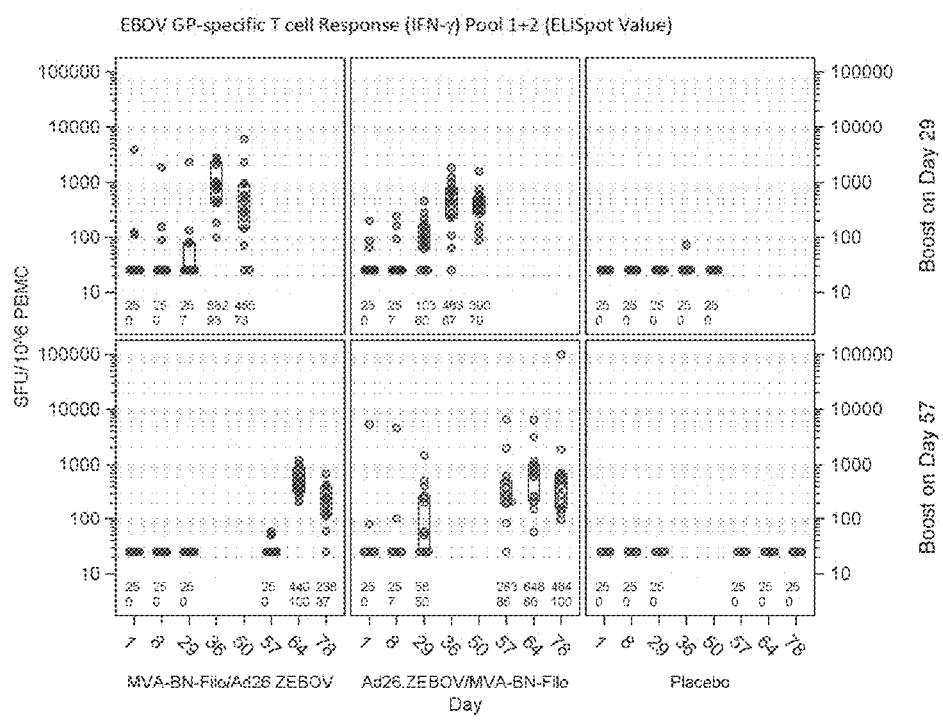

The EBOV GP-specific cellular immune response was measured by interferon gamma (IFN-γ) ELISpot and ICS. To assess the cellular immune response, stored PBMC (peripheral blood mononuclear cells) were thawed and stimulated with peptides organized in 2 pools (Pools 1 and 2). The sum of the T-cell responses stimulated per pool are shown in FIG. 9.

By ELISpot analysis (FIG. 9), an IFN-γ response could readily be detected in 50 to 60% of the subjects at day 29 after prime immunization with Ad26.ZEBOV (median IFN-γ response 103 and 58 spots forming units per million PBMC for Group 3 and 4, respectively) and in 86% of the subjects at day 57 post Ad26.ZEBOV prime immunization (Group 4, median IFN-γ response 283 spots forming units per million (SFU/$10^6$) PBMC). These responses were further boosted by immunization on Day 29 or Day 57 with MVA-BN-Filo (87% responders, median IFN-γ response 463 SFU/$10^6$ PBMC for Group 3, 86% responders, 648 SFU/$10^6$ PBMC for Group 4) and maintained at that level up to day 21 post-boost (79% responders, median IFN-γ response 390 SFU/$10^6$ PBMC for Group 3 and 100% responders, 464 SFU/$10^6$ PBMC for Group 4).

By contrast, only a very low level of EBOV GP-specific IFN-γ secreting cells could be detected post-MVA prime (7% and 0% responders at Day 29 for Group 1 and 2, respectively). However, a strong IFN-γ response was unexpectedly observed peaking at 7 days post-Ad26.ZEBOV boost in 93% and 100% of the subjects boosted at day 29 and day 57, respectively (median IFN-γ response 882 and 440 SFU/$10^6$PBMC), at a level higher than that observed after the Ad26.ZEBOV-prime/MVA-BN-Filo-boost combination using the same time schedule (Group 3 and Group 4).

Results for the cellular assays measuring specific CD4+ and CD8+ T cell responses by ICS are shown in FIGS. 10-15.

Figure 10:
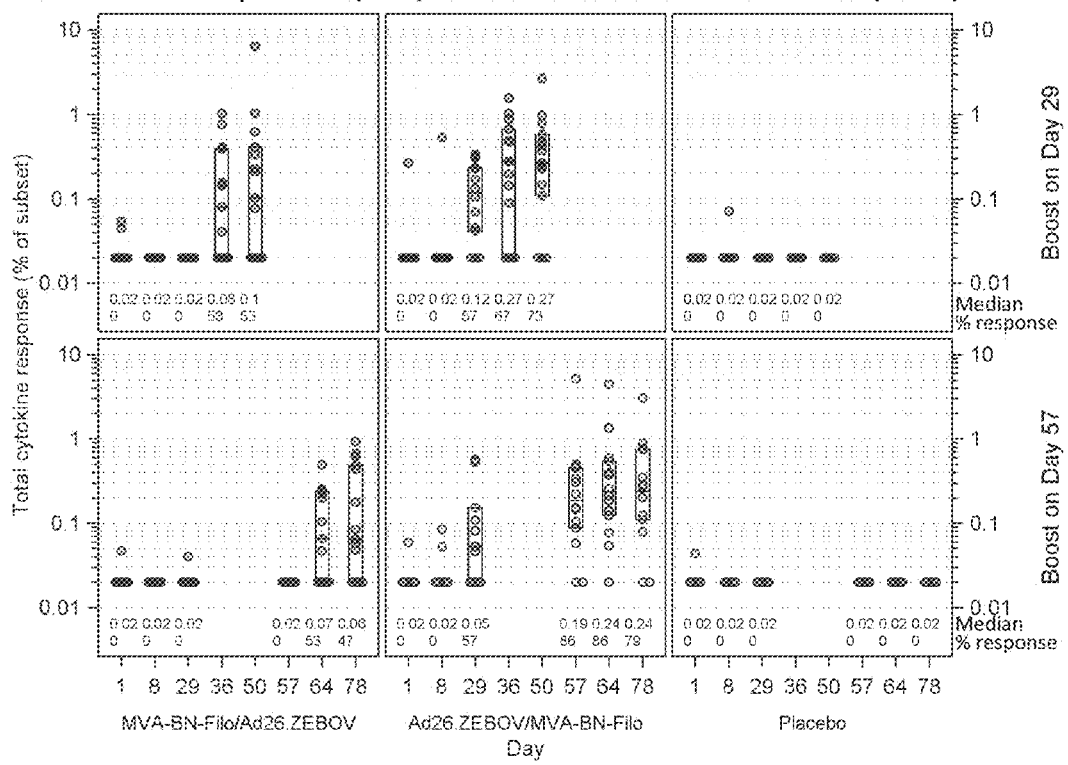
Figure 13:
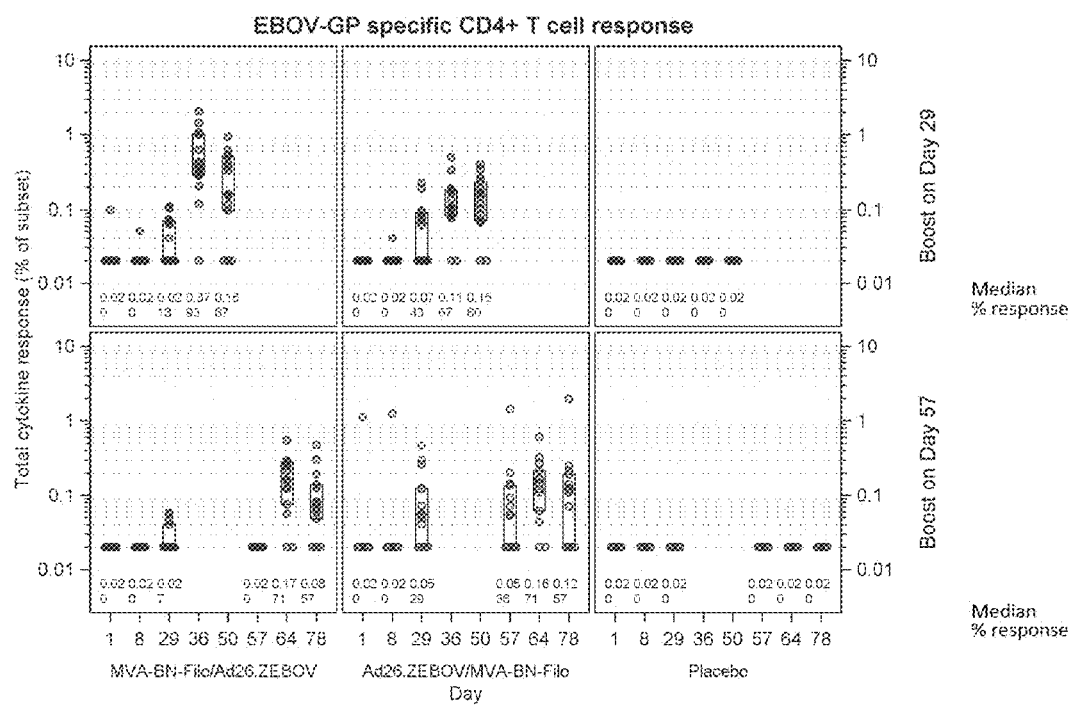

As expected, no EBOV GP-specific CD8+ or CD4+ T cell response was observed in placebo immunized individuals (FIGS. 10 and 13). No CD8+ cytokine responses were observed on Day 29 or Day 57 after prime immunization with MVA-BN-Filo (Group 1 and 2). However, a vaccine-induced CD8+ T cell response was observed in 53% of subjects 7 days post-boost with Ad26.ZEBOV (median total cytokine response: 0.08% and 0.07%, when Ad26 boost immunization administered at day 29 or day 57, respectively; FIG. 10). This response was maintained at day 21 post boost immunization (median total cytokine response: 0.1% and 0.06%, when Ad26 boost immunization administered at day 29 or day 57, respectively; FIG. 10). In comparison, 57% of subjects receiving a prime immunization with Ad26.ZEBOV (Group 3 and Group 4) showed at Day 29 a CD8+ T cell response (median total cytokine response: 0.12 and 0.05%, respectively), 86% of the subjects at day 57 post Ad26.ZEBOV prime immunization (Group 4) showed a CD8+ T cell response (median total cytokine response: 0.19%). This response was further enhanced after boost immunization with MVA-BN-Filo on day 29, with 67% and 73% of subjects responding 7 and 21 days post-boost, respectively (median response: 0.27% on both days).

Figure 11:
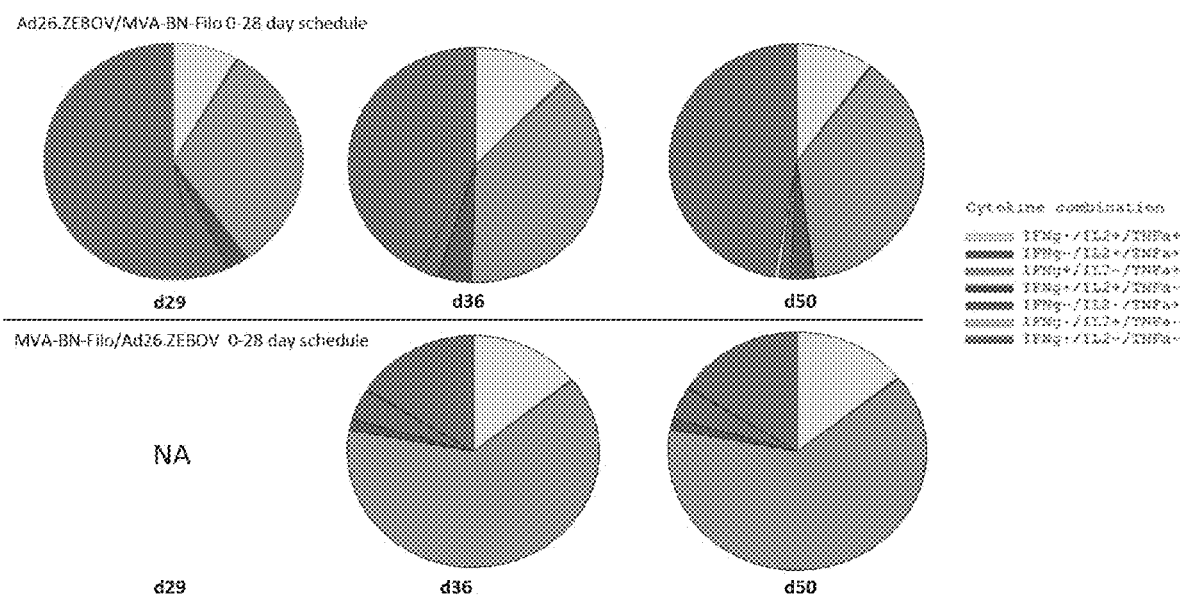

Surprisingly, while a smaller percentage of responders was observed in Group 1 (MVA-Ad26 prime-boost 0-28 day schedule) compared to Group 3 (Ad26-MVA prime-boost 0-28 day schedule), the proportion of polyfunctional CD8+ T cells (CD8+ T cells expressing more than one cytokine) induced by the MVA-Ad26 prime-boost regimen in these responders was higher post-boost than that induced by the Ad26-MVA prime-boost regimen (FIG. 11). This difference was not observed when the prime and boost were administered at day 57. Using this schedule, both the MVA prime Ad26 boost (Group 2) and the Ad26 prime MVA boost (Group 4) regimens induced similarly high proportion of polyfunctional CD8+ T cells (FIG. 12).

Surprisingly, prime immunization with MVA-BN-Filo followed by a boost with Ad26.ZEBOV given at 28 days interval (Group 1) induced a very robust CD4+ T cell response which peaked 7 days post-boost immunization (93% responders, median total cytokine response 0.37%; FIG. 13). At the peak, this CD4+ T cell response was of a higher magnitude than that seen in Group 3 after prime immunization with Ad26.ZEBOV followed by a MVA-BN-Filo boost at 28 days interval (67% responders, median total cytokine response 0.11%). 21 days post-boost, the CD4+ T cell responses induced by both regimens were comparable. Extending the interval of the MVA-BN-Filo/Ad26.ZEBOV regimen to 56 days resulted in lower CD4+ T cell responses. The Ad26.ZEBOV/MVA-BN-Filo regimen induced slightly lower CD4+ T cell responses at a 28-day interval and comparable responses at a 56-day interval. The CD4+ T cells induced by both vaccine combinations were predominantly polyfunctional (FIGS. 14 and 15).

Results of the substudy assessing the immunogenicity of a prime with Ad26.ZEBOV at $5 \times 10^{10}$ vp followed by a boost 14 days later using $1 \times 10^8$ TCID$_{50}$ of MVA-BN-Filo are summarized below.

Overall, this relatively short regimen using a 14-days interval between prime and boost has been shown to be immunogenic. The humoral immune response to vaccinations was assessed by ELISA. As observed for longer intervals, all subjects seroconverted by 21 days post boost immunization (FIG. 16A). Furthermore, a cellular immune response was observed by ELISpot in 92% of the subjects 21 days post boost immunization (FIG. 16B). This cellular immune response consisted of both CD4+ (67% responders, median response 0.08% at day 21 post boost) and CD8+ (64% responders, median response 0.15% at day 7 post boost) specific T cells. The immune response induced using a 2 weeks interval appeared somewhat lower than the response induced when using longer intervals between prime and boost (refer to previous section).

Example 4

A randomized, placebo-controlled, observer-blind study (preceded by an initial open-label vaccination of a total of 6 sentinel study subjects) is performed to evaluate the safety, tolerability and immunogenicity of a heterologous regimen of (a) a single dose of MVA-BN-Filo ($1 \times 10^8$ TCID$_{50}$) or placebo (0.9% saline) as prime followed by a single dose of Ad26.ZEBOV ($5 \times 10^{10}$ vp) or placebo as boost at different time points (14, 28, or 56 days after prime; Groups 1 to 3) and (b) a single dose of Ad26.ZEBOV ($5 \times 10^{10}$ vp) or placebo as prime followed by a single dose of MVA-BN-Filo ($1 \times 10^8$ TCID$_{50}$) or placebo as boost at 28 days after prime (Group 4).

In order to assess the safety of the 2 vaccines independently, Groups 5 and 6 are included where homologous regimens of 2 single doses of MVA-BN-Filo ($1 \times 10^8$ TCID$_{50}$) or placebo, or 2 single doses of Ad26.ZEBOV ($5 \times 10^{10}$ vp) or placebo are administered with the shorter prime-boost schedule of 1 and 15 days. This study is conducted in a target of approximately 92 healthy subjects, aged between 18 and 50 years (inclusive) who have never received an experimental Ebola candidate vaccine before and have no known exposure to or diagnosis of Ebola disease.

The study consists of a vaccination period in which subjects are vaccinated at their baseline visit (Day 1) followed by a boost on Day 15, 29, or 57, and a post-boost follow-up period until all subjects have had their 21-day post-boost visit, or discontinued earlier. At that time, the study will be unblinded.

Subjects are enrolled in 6 different groups, comprising 18 (Groups 1 to 4) or 10 (Groups 5 and 6) healthy subjects each. Within Groups 1 to 4, subjects are randomized in a 5:1 ratio to receive active vaccine or placebo throughout the study. Groups 5 and 6 each start with a Sentinel Cohort of 3 subjects who receive active vaccine in an open-label fashion, followed by a blinded cohort of 7 subjects, who are randomized in a 6:1 ratio to receive active vaccine or placebo.

The study vaccination schedules in the different groups are summarized in Table 6.

TABLE 6

Study Vaccination Schedules

| Group | N | n | Day 1 | Day 15 | Day 29 | Day 57 |
|---|---|---|---|---|---|---|
| 1 | 18 | 15 | MVA-BN-Filo | Ad26.ZEBOV | | |
|   |   | 3 | Placebo | Placebo | | |
| 2 | 18 | 15 | MVA-BN-Filo | | Ad26.ZEBOV | |
|   |   | 3 | Placebo | | Placebo | |

TABLE 6-continued

Study Vaccination Schedules

| Group | N | n | Day 1 | Day 15 | Day 29 | Day 57 |
|---|---|---|---|---|---|---|
| 3 | 18 | 15 | MVA-BN-Filo | | | Ad26.ZEBOV |
| | | 3 | Placebo | | | Placebo |
| 4 | 18 | 15 | Ad26.ZEBOV | | MVA-BN-Filo | |
| | | 3 | Placebo | | Placebo | |
| 5 | 10 | 3 | MVA-BN-Filo (sentinel) | MVA-BN-Filo (sentinel) | | |
| | | 6 | MVA-BN-Filo | MVA-BN-Filo | | |
| | | 1 | Placebo | Placebo | | |
| 6 | 10 | 3 | Ad26.ZEBOV (sentinel) | Ad26.ZEBOV (sentinel) | | |
| | | 6 | Ad26.ZEBOV | Ad26.ZEBOV | | |
| | | 1 | Placebo | Placebo | | |

N: number of subjects to receive study vaccine
MVA-BN-Filo dose level is $1 \times 10^8$ TCID$_{50}$ (50% Tissue Culture Infective Dose) in all groups;
Ad26.ZEBOV dose level is $5 \times 10^{10}$ vp (viral particles) in all groups;
Placebo is 0.9% saline Safety is assessed by collection of solicited local and systemic adverse events, unsolicited adverse events and serious adverse events, and by physical examination. In addition, standard chemistry, hematologic (including coagulation parameters) and urinalysis parameters are assessed at multiple time points.

Immunogenicity is assessed using the immunologic assays summarized in Table 7 and 8. The exploratory assay package may include, but is not limited to, the listed assays.

TABLE 7

Summary of Immunologic Assays (Serology)

| Assay | Purpose |
|---|---|
| Secondary endpoints | |
| Virus neutralization assay | Analysis of neutralizing antibodies to EBOV GP |
| ELISA | Analysis of antibodies binding to EBOV GP |
| Exploratory endpoints | |
| Adenovirus/MVA neutralization assay | Neutralizing antibodies to adenovirus/MVA |
| Molecular antibody characterization | Analysis of anti-EBOV GP, SUDV GP, MARV GP and/or TAFV NP antibody characteristics, including IgG subtyping |
| Exploratory ELISA | Analysis of binding antibodies to a different source of EBOV GP |

EBOV: Ebola virus;
ELISA: enzyme-linked immunosorbent assay;
GP: glycoprotein;
IgG: Immunoglobulin G;
MARV: Marburg virus;
MVA: Modified Vaccinia Ankara;
NP: nucleoprotein;
SUDV: Sudan virus;
TAFV: Taï Forest virus

TABLE 8

Summary of Immunologic Assays (Cellular)

| Assay | Purpose |
|---|---|
| Secondary endpoints | |
| ELISpot | T-cell IFN-γ responses to EBOV GP |
| Exploratory endpoints | |
| ICS of frozen PBMC | Analysis of T-cell responses to EBOV GP, SUDV GP, MARV GP and/or TAFV NP |
| ICS and/or ELISpot of fresh PBMC | (including CD4/8, IL-2, IFN-γ, TNF-α and/or activation markers) Analysis of T cell responses to EBOV GP including CD4-positive and low-magnitude T cell responses |

EBOV: Ebola virus;
ELISpot: enzyme-linked immunospot;
GP: glycoprotein;
ICS: intracellular cytokine staining;
IFN: interferon;
IL: interleukin;
MARV: Marburg virus;
NP: nucleoprotein;
PBMC: peripheral blood mononuclear cells;
SUDV: Sudan virus;
TAFV: Taï Forest virus;
TNF: tumor necrosis factor The clinical study is ongoing. Some of the initial results are described below.

Assessment of Humoral Immune Response

Figure 17:
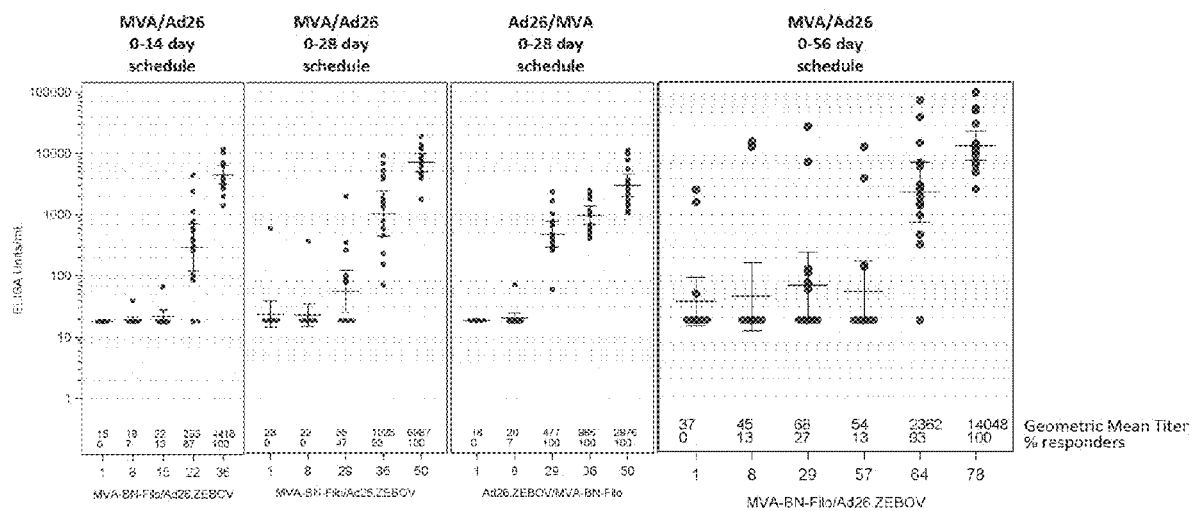

As shown in FIG. 17, all subjects seroconverted 21 days post boost immunization when assessed by ELISA. Similar to previous experiments, a higher immune response was observed at 21 days post boost immunization when MVA was used as a prime and Ad26 administered as a boost 28 days later (Group 2, Geometric Mean Concentration of EU/mL 6987) compared to the reverse order of vaccine immunization (Group 4, Geometric Mean Concentration of EU/mL 2976).

The strength of the humoral immune response correlated with the interval between the prime and the boost, with higher antibody concentrations observed when using a 56 days interval between MVA prime and Ad26 boost (group 3, Geometric Mean Concentration of EU/mL 14048) compared to a shorter schedule (group 1, 14 days interval, Geometric Mean Concentration of EU/mL 4418 and group 2, 28 days interval, Geometric Mean Concentration of EU/mL 6987).

Surprisingly, a robust humoral immune response as assessed by ELISA was observed when MVA-BN-Filo was used as a prime and followed by a boost immunization with Ad26.ZEBOV 14 days later. All subjects receiving the vaccine regimen seroconverted by 21 days post boost immunization, and the antibody concentration at this time point reached similar or higher levels than when using the Ad26 prime MVA boost combination at a 28 day intervals (Geometric Mean Titer of EU/mL 4418 and 2976, respectively). Surprisingly, the antibody concentrations induced by this MVA/Ad26 prime boost combination at 14 days interval Were strikingly higher than the response induced by the reverse vaccine regimen at the same prime-boost time interval (refer to example 2, FIG. 16A, Geometric Mean Concentration of EU/mL 915). This confirms the induction of a robust immune response by an MVA prime Ad26 boost combination and the advantage of such combination when using a short prime boost interval (14 days).

Assessment of Cellular Immune Response

Figure 18:
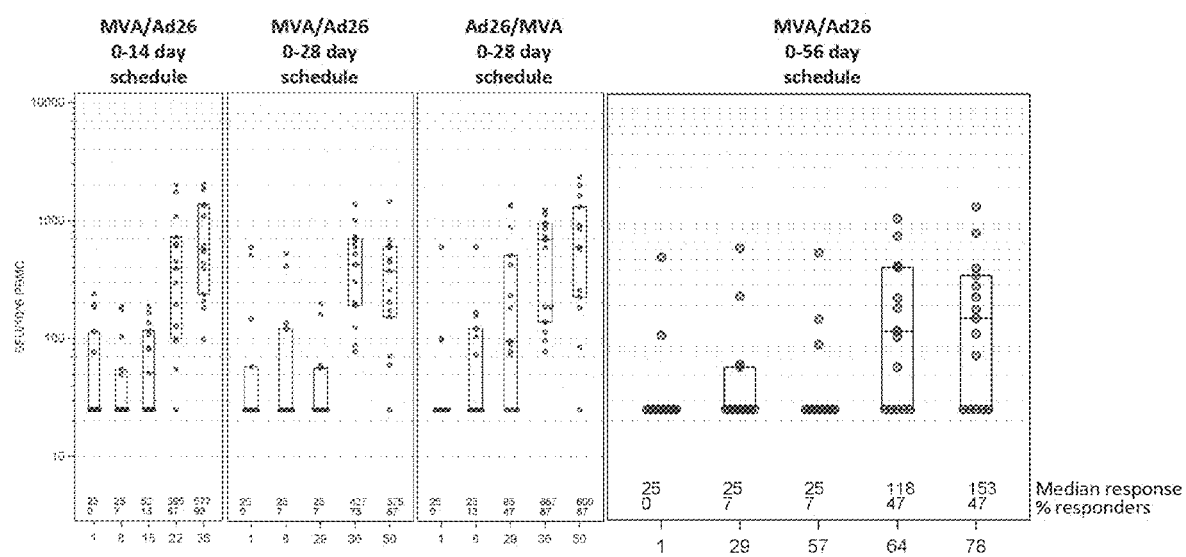
Figure 19:
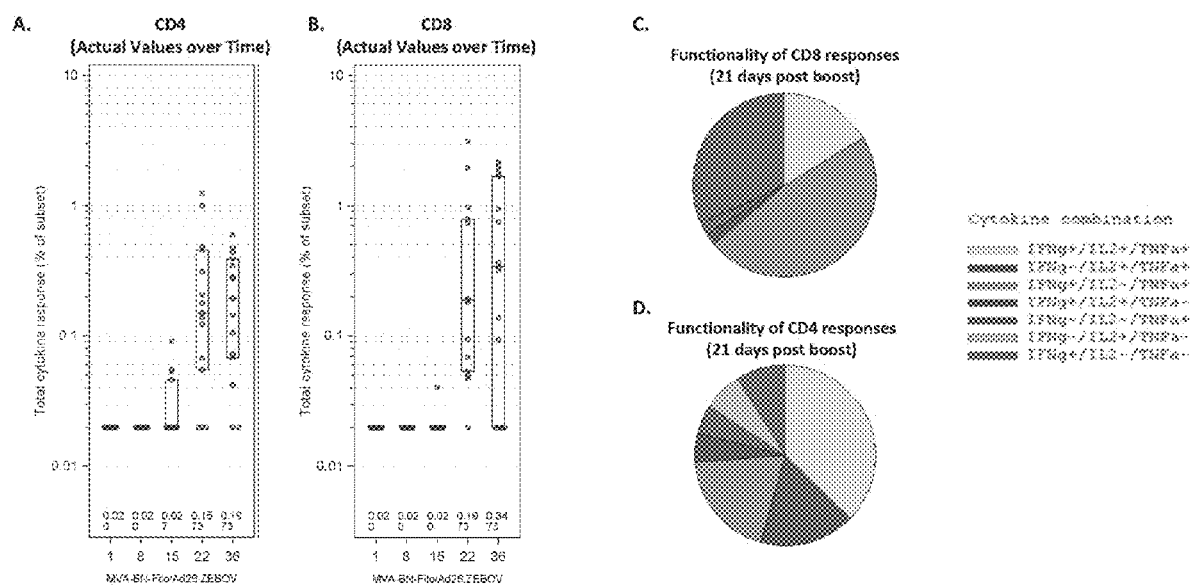

The EBOV GP-specific cellular immune response was measured by interferon gamma (IFN-γ) ELISpot and ICS. To assess the cellular immune response, stored PBMC (peripheral blood mononuclear cells) were thawed and stimulated with peptides organized in 2 pools (Pools 1 and 2). The sum of the T cell responses stimulated per pool are shown in FIGS. 18-19.

0.34% at day 7 and 21 post boost, respectively; FIGS. 19 A and B). Both the CD8+ and CD4+ T cells induced by this vaccine combination were predominantly polyfunctional (FIGS. 19 C and D).

Figure 16:
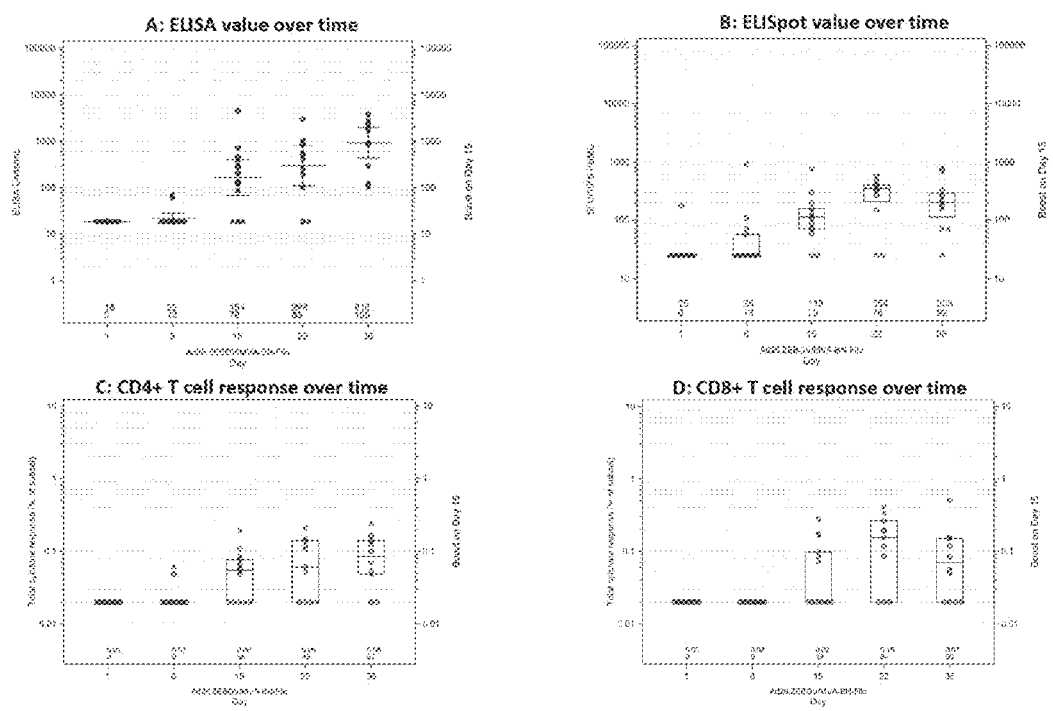

Unexpectedly, the cellular immune response induced by this MVA/Ad26 prime boost combination at 14 days interval were strikingly higher than the response induced by the reverse vaccine regimen using the same prime-boost interval (refer to example 2, FIGS. 16 B, C and D). This confirms the potential of an MVA prime Ad26 boost combination when using a short prime boost time interval (14 days).

The following tables 9-12 are presented as summaries of the clinical studies presented herein. The studies presented in example 3 and 4 are numbered study 1001 and 1002 respectively.

Table 9 is a summary of the humoral immune responses as determined in ELISA assays during the studies as described in example 3 and 4.

TABLE 9

Overview of ELISA titers in clinical studies

| Study Day | Ad26/ MVA 0, 14 | Ad26/ MVA 0, 28 | Ad26/ MVA 0, 28 | Ad26/ MVA 0, 56 | MVA/ Ad26 0, 14 | MVA/ Ad26 0, 28 | MVA/ Ad26 0, 28 | MVA/ Ad26 0, 56 |
|---|---|---|---|---|---|---|---|---|
| Study | 1001 | 1001 | 1002 | 1001 | 1002 | 1001 | 1002 | 1001 |
| d8 | 22 (13) | 18 (0) | 20 (7) | 22 (0) | 19 (7) | 18 (0) | 22 (0) | 21 (0) |
| d15 | 164 (79)* | — | — | — | 22 (13)* | — | — | — |
| d22 | 298 (83) | — | — | — | 293 (87) | — | — | — |
| d29 | — | 533 (93)* | 477 (100)* | 582 (100)* | — | 36 (40)* | 55 (47)* | 22 (7) |
| d36 | 915 (100) | 946 (100) | 965 (100) | — | 4418 (100) | 269 (80) | 1025 (93) | — |
| d50 | — | 4274 (100) | 2976 (100) | — | — | 10573 (100) | 6987 (100) | — |
| d57 | — | — | — | 854 (100)* | — | — | — | 21 (7)* |
| d64 | — | — | — | 1554 (100) | — | — | — | 568 (100) |
| d78 | — | — | — | 7553 (100) | — | — | — | 18729 (100) |

The data are presented as geometric mean concentration (GMC) in ELISA per mL.
Percentage of responders at each time points is indicated in brackets;.
Ad26: Immunization with Ad26.ZEBOV;
MVA: Immunization with MVA-BN-Filo;
Prime boost schedule is indicated in headers.
0, 14: 14 days interval between prime and boost immunizations;
0, 28: 28 days interval between prime and boost immunizations;
0, 56: 56 days interval between prime and boost immunizations;
*day of boost;
GMC: Geometric Mean Concentration.
Study 1001 was described in example 3 and study 1002 was described in example 4.

Surprisingly, when using MVA-BN-Filo as a prime followed by Ad26.ZEBOV as a boost, a stronger IFN-γ response was observed when using a shorter 14 days interval between prime and boost (87 and 93% responders, 395 and 577 SFU/10⁶ PBMC for Group 1 at day 7 and 21 post boost, respectively) compared to the response induced by a 28 days (Group 2, 73 and 67% responders, median IFN-γ response 427 and 375 SFU/10⁶ PBMC for day 7 and day 21 post boost) or 56 days interval (Group 3, 47% responders, median IFN-γ response 118 and 153 SFU/10⁶ PBMC for day 7 and day 21 post boost).

Remarkably, the cellular immune response induced by the MVA-BN-Filo prime Ad26.ZEBOV boost at a 14 days interval was well balanced with both EBOV GP-specific CD8+ and CD4+ T cell response (73% responders for both CD4+ and CD8+ T cells, CD4+ median total cytokine response 0.15 and 0.19% at day 7 and 21 post boost, respectively; CD8+ median total cytokine response 0.19 and Table 10 is a summary of the cellular immune responses as determined in ELISpot assays during the studies as described in example 3 and 4.

TABLE 10

Overview of cellular immune responses in clinical studies as determined by ELISpot

| Study Day | Ad26/ MVA 0, 14 | Ad26/ MVA 0, 28 | Ad26/ MVA 0, 56 | MVA/ Ad26 0, 14 | MVA/ Ad26 0, 28 | MVA/ Ad26 0, 56 |
|---|---|---|---|---|---|---|
| Study | 1001 | 1001 | 1001 | 1002 | 1001 | 1001 |
| d8 | 25 (13) | 25 (7) | 25 (7) | 25 (13) | 25 (0) | 25 (0) |
| d15 | 113 (79)* | — | — | 52 (20)* | — | — |
| d22 | 354 (75) | — | — | 293 (87) | — | — |
| d29 | — | 103 (60)* | 58 (50) | — | 25 (7)* | 25 (0) |
| d36 | 203 (92) | 463 (87) | — | 552 (100) | 882 (93) | — |
| d50 | — | 390 (79) | — | — | 455 (73) | — |
| d57 | — | — | 243 (86)* | — | — | 25 (0)* |

TABLE 10-continued

Overview of cellular immune responses in clinical studies as determined by ELISpot

| Study Day | Ad26/ MVA 0, 14 | Ad26/ MVA 0, 28 | Ad26/ MVA 0, 56 | MVA/ Ad26 0, 14 | MVA/ Ad26 0, 28 | MVA/ Ad26 0, 56 |
|---|---|---|---|---|---|---|
| d64 | — | — | 648 (86) | — | — | 440 (100) |
| d78 | — | — | 464 (100) | — | — | 238 (87) |

Data are represented as median SFU/10$^6$ PBMC.
Percentage of responders at each time points is indicated in brackets;
Ad26: Immunization with Ad26.ZEBOV;
MVA: Immunization with MVA-BN-Filo;
Prime boost schedule is indicated in headers.
0, 14: 14 days interval between prime and boost immunizations;
0, 28: 28 days interval between prime and boost immunizations;
0, 56: 56 days interval between prime and boost immunizations;
*day of boost;
SFU: Spot Forming Units;
PBMC: Peripheral blood mononuclear cells.
Study 1001 was described in example 3 and study 1002 was described in example 4.

Table 11 is a summary of CD4+ T cell responses as determined by intracellular cytokine staining (ICS) during the studies as described in example 3 and 4.

TABLE 11

Overview of the CD4+ T cell immune response as measured by ICS in clinical studies

| Study Day | Ad26/ MVA 0, 14 | Ad26/ MVA 0, 28 | Ad26/ MVA 0, 56 | MVA/ Ad26 0, 14 | MVA/ Ad26 0, 28 | MVA/ Ad26 0, 56 |
|---|---|---|---|---|---|---|
| Study | 1001 | 1001 | 1001 | 1002 | 1001 | 1001 |
| d8 | 0.02 (0) | 0.02 (0) | 0.02 (0) | 0.02 (0) | 0.02 (0) | 0.02 (0) |
| d15 | 0.06 (36)* | — | — | 0.02 (7)* | — | — |
| d22 | 0.06 (45) | — | — | 0.15 (73) | — | — |
| d29 | — | 0.07 (43)* | 0.06 (31) | — | 0.02 (13)* | 0.02 (7) |
| d36 | 0.08 (67) | 0.11 (64) | — | 0.19 (73) | 0.37 (93) | — |
| d50 | — | 0.15 (60) | — | — | 0.16 (67) | — |
| d57 | — | — | 0.05 (36)* | — | — | 0.02 (0)* |
| d64 | — | — | 0.16 (71) | — | — | 0.17 (67) |
| d78 | — | — | 0.12 (57) | — | — | 0.08 (53) |

Data are represented as median total CD4+ cytokine response in %.
Percentage of responders at each time points is indicated in brackets;
Ad26: Immunization with Ad26.ZEBOV;
MVA: Immunization with MVA-BN-Filo;
Prime boost schedule is indicated in headers.
0, 14: 14 days interval between prime and boost immunizations;
0, 28: 28 days interval between prime and boost immunizations;
0, 56: 56 days interval between prime and boost immunizations;
*day of boost.
Study 1001 was described in example 3 and study 1002 was described in example 4.

Table 12 is a summary of CD8+ T cell responses as determined by intracellular cytokine staining (ICS) during the studies as described in example 3 and 4.

TABLE 12

Overview of the CD8+ T cell immune response as measured by ICS in clinical studies

| Study Day | Ad26/ MVA 0, 14 | Ad26/ MVA 0, 28 | Ad26/ MVA 0, 56 | MVA/ Ad26 0, 14 | MVA/ Ad26 0, 28 | MVA/ Ad26 0, 56 |
|---|---|---|---|---|---|---|
| Study | 1001 | 1001 | 1001 | 1002 | 1001 | 1001 |
| d8 | 0.02 (0) | 0.02 (0) | 0.02 (0) | 0.02 (0) | 0.02 (0) | 0.02 (0) |
| d15 | 0.02 (29)* | — | — | 0.02 (0)* | — | — |
| d22 | 0.15 (64) | — | — | 0.19 (73) | — | — |
| d29 | — | 0.12 (57)* | 0.05 (57) | — | 0.02 (0)* | 0.02 (0) |
| d36 | 0.07 (50) | 0.27 (67) | — | 0.34 (73) | 0.08 (53) | — |
| d50 | — | 0.27 (73) | — | — | 0.01 (53) | — |
| d57 | — | — | 0.19 (86)* | — | — | 0.02 (0)* |
| d64 | — | — | 0.24 (86) | — | — | 0.07 (53) |
| d78 | — | — | 0.24 (79) | — | — | 0.06 (47) |

Data are presented as median total CD8+ cytokine response in %.
Percentage of responders at each time points is indicated in brackets;.
Ad26: Immunization with Ad26.ZEBOV;
MVA: Immunization with MVA-BN-Filo;

TABLE 12-continued

Overview of the CD8+ T cell immune response as measured by ICS in clinical studies

| Study Day | Ad26/ MVA 0, 14 | Ad26/ MVA 0, 28 | Ad26/ MVA 0, 56 | MVA/ Ad26 0, 14 | MVA/ Ad26 0, 28 | MVA/ Ad26 0, 56 |
|---|---|---|---|---|---|---|

Prime boost schedule is indicated in headers.
0, 14: 14 days interval between prime and boost immunizations:
0, 28: 28 days interval between prime and boost immunizations;
0, 56: 56 days interval between prime and boost immunizations:
*day of boost.
Study 1001 was described in example 3 and study 1002 was described in example 4.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A method of enhancing an immune response against at least one filovirus subtype in a human subject, the method comprising:

a. administering to the human subject a first composition comprising an immunologically effective amount of an MVA vector comprising a first polynucleotide encoding an antigenic protein of at least one filovirus subtype, a substantially similar antigenic protein, or an immunogenic polypeptide thereof for priming the immune response; and b. administering to the subject a second composition comprising an immunologically effective amount of an adenovirus vector comprising a second polynucleotide encoding the antigenic protein of at least one filovirus subtype, a substantially similar antigenic protein, or an immunogenic polypeptide thereof for boosting the immune response;

to thereby obtain an enhanced immune response against the antigenic protein in the human subject.

2. The method according to claim 1, wherein the enhanced immune response comprises an enhanced antibody response against the antigenic protein in the human subject.

3. The method according to claim 1, wherein the enhanced immune response comprises an enhanced CD8+ T cell response against the antigenic protein in the human subject.

4. The method according to claim 1, wherein the enhanced immune response comprises an enhanced CD4+ T cell response against the antigenic protein in the human subject.

5. The method according to claim 1, wherein the enhanced immune response comprises an enhanced CD8+ T cell response or an enhanced CD4+ T cell response, and wherein the enhanced CD8+ or CD4+ T cell response comprises an increase or induction of a dominant CD8+ or CD4+ T cell response against the antigenic protein in the human subject.

6. The method according to claim 1, wherein the enhanced immune response comprises an enhanced CD8+ T cell response or an enhanced CD4+ T cell response, and wherein the enhanced CD8+ or CD4+ T cell response comprises an increase or induction of polyfunctional CD8+ or CD4+ T cells specific to the antigenic protein in the human subject.

7. The method according to claim 2, wherein the enhanced immune response further comprises an enhanced CD8+ T cell response and an enhanced CD4+ T cell response against the antigenic protein in the human subject.

8. The method according to claim 7, wherein the enhanced CD8+ and CD4+ T cell response comprises an increase or induction of polyfunctional CD4+ and CD8+ T cells specific to the antigenic protein in the human subject.

9. The method according to claim 1, wherein the enhanced immune response comprises an enhanced CD4+ T cell response, an enhanced antibody response and an enhanced CD8+ T cell response, against the antigenic protein in the human subject.

10. The method according to claim 1, wherein the enhanced immune response provides a protective immunity to the human subject against a disease related to the antigenic protein.

11. The method according to claim 1, wherein the adenovirus vector is an rAd26 vector.

12. The method according to claim 1, wherein step (b) is conducted 1-12 weeks after step (a).

13. The method according to claim 1, wherein step (b) is conducted 2-12 weeks after step (a).

14. The method according to claim 1, wherein step (b) is conducted at least 1 weeks after step (a).

15. The method according to claim 1, wherein step (b) is conducted at least 2 weeks after step (a).

16. The method according to claim 1, wherein the antigenic protein comprises the amino acid sequence selected from the group consisting of SEQ ID NO: 1, SEQ ID NO: 2, SEQ ID NO: 3, SEQ ID NO: 4, and SEQ ID NO: 5.

17. The method according to claim 16, wherein the MVA vector comprises a polynucleotide encoding the antigenic proteins having the amino acid sequences of SEQ ID NO: 1, SEQ ID NO: 2, SEQ ID NO: 4, and SEQ ID NO: 5.

18. The method according to claim 16, wherein the adenovirus vector comprises a polynucleotide encoding at least one antigenic protein having the amino acid sequence of SEQ ID NO: 1, SEQ ID NO: 2, or SEQ ID NO: 3.

19. The method according to claim 16, wherein the adenovirus vector comprises a polynucleotide encoding the antigenic protein having the amino acid sequence of SEQ ID NO: 1.

20. The method according to claim 19, wherein the adenovirus vector is an rAd26 vector.

* * * * *

```
                        SEQUENCE LISTING

<160> NUMBER OF SEQ ID NOS: 5

<210> SEQ ID NO 1
<211> LENGTH: 676
<212> TYPE: PRT
<213> ORGANISM: Artificial Sequence
<220> FEATURE:
<223> OTHER INFORMATION: Glycoprotein Ebola virus Zaire, strain Mayinga

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240
```

```
Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
```

-continued

```
                660                 665                 670
Lys Phe Val Phe
            675

<210> SEQ ID NO 2
<211> LENGTH: 676
<212> TYPE: PRT
<213> ORGANISM: Artificial Sequence
<220> FEATURE:
<223> OTHER INFORMATION: Glycoprotein Ebola virus Sudan, strain Gulu

<400> SEQUENCE: 2

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
    290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
```

```
                    340                 345                 350
Leu His Ile Pro Glu Gly Glu Thr Thr Leu Pro Ser Gln Asn Ser Thr
                355                 360                 365

Glu Gly Arg Arg Val Gly Val Asn Thr Gln Glu Thr Ile Thr Glu Thr
            370                 375                 380

Ala Ala Thr Ile Ile Gly Thr Asn Gly Asn His Met Gln Ile Ser Thr
385                 390                 395                 400

Ile Gly Ile Arg Pro Ser Ser Ser Gln Ile Pro Ser Ser Ser Pro Thr
                405                 410                 415

Thr Ala Pro Ser Pro Glu Ala Gln Thr Pro Thr Thr His Thr Ser Gly
            420                 425                 430

Pro Ser Val Met Ala Thr Glu Glu Pro Thr Thr Pro Pro Gly Ser Ser
        435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Thr Asn Thr Lys Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675

<210> SEQ ID NO 3
<211> LENGTH: 681
<212> TYPE: PRT
<213> ORGANISM: Artificial Sequence
<220> FEATURE:
<223> OTHER INFORMATION: Glycoprotein Marburg virus Angola

<400> SEQUENCE: 3

Met Lys Thr Thr Cys Leu Leu Ile Ser Leu Ile Leu Ile Gln Gly Val
1               5                   10                  15

Lys Thr Leu Pro Ile Leu Glu Ile Ala Ser Asn Ile Gln Pro Gln Asn
```

```
                20              25              30
Val Asp Ser Val Cys Ser Gly Thr Leu Gln Lys Thr Glu Asp Val His
            35              40              45
Leu Met Gly Phe Thr Leu Ser Gly Gln Lys Val Ala Asp Ser Pro Leu
        50              55              60
Glu Ala Ser Lys Arg Trp Ala Phe Arg Ala Gly Val Pro Pro Lys Asn
65              70              75              80
Val Glu Tyr Thr Glu Gly Glu Ala Lys Thr Cys Tyr Asn Ile Ser
                85              90              95
Val Thr Asp Pro Ser Gly Lys Ser Leu Leu Asp Pro Pro Thr Asn
            100             105             110
Ile Arg Asp Tyr Pro Lys Cys Lys Thr Ile His His Ile Gln Gly Gln
            115             120             125
Asn Pro His Ala Gln Gly Ile Ala Leu His Leu Trp Gly Ala Phe Phe
            130             135             140
Leu Tyr Asp Arg Ile Ala Ser Thr Thr Met Tyr Arg Gly Lys Val Phe
145             150             155             160
Thr Glu Gly Asn Ile Ala Ala Met Ile Val Asn Lys Thr Val His Lys
                165             170             175
Met Ile Phe Ser Arg Gln Gly Gln Gly Tyr Arg His Met Asn Leu Thr
            180             185             190
Ser Thr Asn Lys Tyr Trp Thr Ser Ser Asn Gly Thr Gln Thr Asn Asp
            195             200             205
Thr Gly Cys Phe Gly Thr Leu Gln Glu Tyr Asn Ser Thr Lys Asn Gln
            210             215             220
Thr Cys Ala Pro Ser Lys Lys Pro Leu Pro Leu Pro Thr Ala His Pro
225             230             235             240
Glu Val Lys Leu Thr Ser Thr Ser Thr Asp Ala Thr Lys Leu Asn Thr
                245             250             255
Thr Asp Pro Asn Ser Asp Asp Glu Asp Leu Thr Thr Ser Gly Ser Gly
            260             265             270
Ser Gly Glu Gln Glu Pro Tyr Thr Thr Ser Asp Ala Ala Thr Lys Gln
            275             280             285
Gly Leu Ser Ser Thr Met Pro Pro Thr Pro Ser Pro Gln Pro Ser Thr
            290             295             300
Pro Gln Gln Gly Gly Asn Asn Thr Asn His Ser Gln Gly Val Val Thr
305             310             315             320
Glu Pro Gly Lys Thr Asn Thr Thr Ala Gln Pro Ser Met Pro Pro His
                325             330             335
Asn Thr Thr Thr Ile Ser Thr Asn Asn Thr Ser Lys His Asn Leu Ser
            340             345             350
Thr Pro Ser Val Pro Ile Gln Asn Ala Thr Asn Tyr Asn Thr Gln Ser
            355             360             365
Thr Ala Pro Glu Asn Glu Gln Thr Ser Ala Pro Ser Lys Thr Thr Leu
            370             375             380
Leu Pro Thr Glu Asn Pro Thr Thr Ala Lys Ser Thr Asn Ser Thr Lys
385             390             395             400
Ser Pro Thr Thr Thr Val Pro Asn Thr Thr Asn Lys Tyr Ser Thr Ser
                405             410             415
Pro Ser Pro Thr Pro Asn Ser Thr Ala Gln His Leu Val Tyr Phe Arg
            420             425             430
Arg Lys Arg Asn Ile Leu Trp Arg Glu Gly Asp Met Phe Pro Phe Leu
            435             440             445
```

```
Asp Gly Leu Ile Asn Ala Pro Ile Asp Phe Asp Pro Val Pro Asn Thr
            450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
                    485                 490                 495

Lys Val Asn Glu Asn Thr Ala His Ser Gly Glu Asn Glu Asn Asp Cys
                500                 505                 510

Asp Ala Glu Leu Arg Ile Trp Ser Val Gln Glu Asp Leu Ala Ala
            515                 520                 525

Gly Leu Ser Trp Ile Pro Phe Phe Gly Pro Gly Ile Glu Gly Leu Tyr
            530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
                565                 570                 575

Thr Thr Glu Glu Arg Thr Phe Ser Leu Ile Asn Arg His Ala Ile Asp
                580                 585                 590

Phe Leu Leu Ala Arg Trp Gly Gly Thr Cys Lys Val Leu Gly Pro Asp
            595                 600                 605

Cys Cys Ile Gly Ile Glu Asp Leu Ser Arg Asn Ile Ser Glu Gln Ile
            610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
                660                 665                 670

Cys Arg Ile Phe Thr Lys Tyr Ile Gly
            675                 680

<210> SEQ ID NO 4
<211> LENGTH: 681
<212> TYPE: PRT
<213> ORGANISM: Artificial Sequence
<220> FEATURE:
<223> OTHER INFORMATION: Glycoprotein Marburg virus Musoke

<400> SEQUENCE: 4

Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
                20                  25                  30

Val Asp Ser Val Cys Ser Gly Thr Leu Gln Lys Thr Glu Asp Val His
            35                  40                  45

Leu Met Gly Phe Thr Leu Ser Gly Gln Lys Val Ala Asp Ser Pro Leu
        50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125
```

```
Asn Pro His Ala Gln Gly Ile Ala Leu His Leu Trp Gly Ala Phe Phe
    130                 135                 140
Leu Tyr Asp Arg Ile Ala Ser Thr Thr Met Tyr Arg Gly Lys Val Phe
145                 150                 155                 160
Thr Glu Gly Asn Ile Ala Ala Met Ile Val Asn Lys Thr Val His Lys
                    165                 170                 175
Met Ile Phe Ser Arg Gln Gly Gln Gly Tyr Arg His Met Asn Leu Thr
                180                 185                 190
Ser Thr Asn Lys Tyr Trp Thr Ser Ser Asn Gly Thr Gln Thr Asn Asp
        195                 200                 205
Thr Gly Cys Phe Gly Ala Leu Gln Glu Tyr Asn Ser Thr Lys Asn Gln
        210                 215                 220
Thr Cys Ala Pro Ser Lys Ile Pro Pro Leu Pro Thr Ala Arg Pro
225                 230                 235                 240
Glu Ile Lys Leu Thr Ser Thr Pro Thr Asp Ala Thr Lys Leu Asn Thr
                    245                 250                 255
Thr Asp Pro Ser Ser Asp Asp Glu Asp Leu Ala Thr Ser Gly Ser Gly
                260                 265                 270
Ser Gly Glu Arg Glu Pro His Thr Thr Ser Asp Ala Val Thr Lys Gln
        275                 280                 285
Gly Leu Ser Ser Thr Met Pro Pro Thr Pro Ser Pro Gln Pro Ser Thr
        290                 295                 300
Pro Gln Gln Gly Gly Asn Asn Thr Asn His Ser Gln Asp Ala Val Thr
305                 310                 315                 320
Glu Leu Asp Lys Asn Asn Thr Thr Ala Gln Pro Ser Met Pro Pro His
                    325                 330                 335
Asn Thr Thr Thr Ile Ser Thr Asn Asn Thr Ser Lys His Asn Phe Ser
                340                 345                 350
Thr Leu Ser Ala Pro Leu Gln Asn Thr Thr Asn Asp Asn Thr Gln Ser
        355                 360                 365
Thr Ile Thr Glu Asn Glu Gln Thr Ser Ala Pro Ser Ile Thr Thr Leu
        370                 375                 380
Pro Pro Thr Gly Asn Pro Thr Thr Ala Lys Ser Thr Ser Ser Lys Lys
385                 390                 395                 400
Gly Pro Ala Thr Thr Ala Pro Asn Thr Thr Asn Glu His Phe Thr Ser
                    405                 410                 415
Pro Pro Pro Thr Pro Ser Ser Thr Ala Gln His Leu Val Tyr Phe Arg
                420                 425                 430
Arg Lys Arg Ser Ile Leu Trp Arg Glu Gly Asp Met Phe Pro Phe Leu
        435                 440                 445
Asp Gly Leu Ile Asn Ala Pro Ile Asp Phe Asp Pro Val Pro Asn Thr
        450                 455                 460
Lys Thr Ile Phe Asp Glu Ser Ser Ser Gly Ala Ser Ala Glu Glu
465                 470                 475                 480
Asp Gln His Ala Ser Pro Asn Ile Ser Leu Thr Leu Ser Tyr Phe Pro
                    485                 490                 495
Asn Ile Asn Glu Asn Thr Ala Tyr Ser Gly Glu Asn Glu Asn Asp Cys
                500                 505                 510
Asp Ala Glu Leu Arg Ile Trp Ser Val Gln Glu Asp Leu Ala Ala
        515                 520                 525
Gly Leu Ser Trp Ile Pro Phe Phe Gly Pro Gly Ile Glu Gly Leu Tyr
        530                 535                 540
```

```
Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
            565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
            595                 600                 605

Cys Cys Ile Gly Ile Glu Asp Leu Ser Lys Asn Ile Ser Glu Gln Ile
610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
            645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
            675                 680

<210> SEQ ID NO 5
<211> LENGTH: 739
<212> TYPE: PRT
<213> ORGANISM: Artificial Sequence
<220> FEATURE:
<223> OTHER INFORMATION: Nucleoprotein Ebola virus Tai Forest / Ivory
      coast

<400> SEQUENCE: 5

Met Glu Ser Arg Ala His Lys Ala Trp Met Thr His Thr Ala Ser Gly
1               5                   10                  15

Phe Glu Thr Asp Tyr His Lys Ile Leu Thr Ala Gly Leu Ser Val Gln
            20                  25                  30

Gln Gly Ile Val Arg Gln Arg Val Ile Gln Val His Gln Val Thr Asn
        35                  40                  45

Leu Glu Glu Ile Cys Gln Leu Ile Ile Gln Ala Phe Glu Ala Gly Val
50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
            85                  90                  95

Lys Tyr Leu Glu Gly His Gly Phe Arg Phe Glu Val Arg Lys Lys Glu
        100                 105                 110

Gly Val Lys Arg Leu Glu Glu Leu Leu Pro Ala Ala Ser Ser Gly Lys
    115                 120                 125

Ser Ile Arg Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
            165                 170                 175

Gln Val His Ser Glu Gln Gly Leu Ile Gln Tyr Pro Thr Ala Trp Gln
        180                 185                 190

Ser Val Gly His Met Met Val Ile Phe Arg Leu Met Arg Thr Asn Phe
    195                 200                 205

Leu Ile Lys Phe Leu Leu Ile His Gln Gly Met His Met Val Ala Gly
210                 215                 220
```

```
His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
            245                 250                 255

Lys Thr Glu His Gly Val Arg Leu His Pro Leu Ala Arg Thr Ala Lys
        260                 265                 270

Val Lys Asn Glu Val Asn Ser Phe Lys Ala Ala Leu Ser Ser Leu Ala
    275                 280                 285

Gln His Gly Glu Tyr Ala Pro Phe Ala Arg Leu Leu Asn Leu Ser Gly
290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
            325                 330                 335

Gly Glu Gln Tyr Gln Gln Leu Arg Glu Ala Ala Thr Glu Ala Glu Lys
        340                 345                 350

Gln Leu Gln Lys Tyr Ala Glu Ser Arg Glu Leu Asp His Leu Gly Leu
    355                 360                 365

Asp Asp Gln Glu Lys Lys Ile Leu Lys Asp Phe His Gln Lys Lys Asn
370                 375                 380

Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Thr Leu Leu Lys
            405                 410                 415

Thr Gly Lys Gln Tyr Asp Asp Asp Asn Asp Ile Pro Phe Pro Gly Pro
        420                 425                 430

Ile Asn Asp Asn Glu Asn Ser Glu Gln Gln Asp Asp Pro Thr Asp
    435                 440                 445

Ser Gln Asp Thr Thr Ile Pro Asp Ile Val Asp Pro Asp Asp Gly
450                 455                 460

Arg Tyr Asn Asn Tyr Gly Asp Tyr Pro Ser Glu Thr Ala Asn Ala Pro
465                 470                 475                 480

Glu Asp Leu Val Leu Phe Asp Leu Glu Asp Gly Asp Glu Asp Asp His
            485                 490                 495

Arg Pro Ser Ser Ser Glu Asn Asn Asn Lys His Ser Leu Thr Gly
        500                 505                 510

Thr Asp Ser Asn Lys Thr Ser Asn Trp Asn Arg Asn Pro Thr Asn Met
    515                 520                 525

Pro Lys Lys Asp Ser Thr Gln Asn Asn Asp Asn Pro Ala Gln Arg Ala
530                 535                 540

Gln Glu Tyr Ala Arg Asp Asn Ile Gln Asp Thr Pro Thr Pro His Arg
545                 550                 555                 560

Ala Leu Thr Pro Ile Ser Glu Glu Thr Gly Ser Asn Gly His Asn Glu
            565                 570                 575

Asp Asp Ile Asp Ser Ile Pro Pro Leu Glu Ser Asp Glu Glu Asn Asn
        580                 585                 590

Thr Glu Thr Thr Ile Thr Thr Thr Lys Asn Thr Thr Ala Pro Pro Ala
    595                 600                 605

Pro Val Tyr Arg Ser Asn Ser Glu Lys Glu Pro Leu Pro Gln Glu Lys
610                 615                 620

Ser Gln Lys Gln Pro Asn Gln Val Ser Gly Ser Glu Asn Thr Asp Asn
625                 630                 635                 640
```

-continued

```
Lys Pro His Ser Glu Gln Ser Val Glu Glu Met Tyr Arg His Ile Leu
                645                 650                 655

Gln Thr Gln Gly Pro Phe Asp Ala Ile Leu Tyr Tyr Tyr Met Met Thr
            660                 665                 670

Glu Glu Pro Ile Val Phe Ser Thr Ser Asp Gly Lys Glu Tyr Val Tyr
        675                 680                 685

Pro Asp Ser Leu Glu Gly Glu His Pro Pro Trp Leu Ser Glu Lys Glu
    690                 695                 700

Ala Leu Asn Glu Asp Asn Arg Phe Ile Thr Met Asp Asp Gln Gln Phe
705                 710                 715                 720

Tyr Trp Pro Val Met Asn His Arg Asn Lys Phe Met Ala Ile Leu Gln
                725                 730                 735

His His Lys
```